US010796715B1

(12) United States Patent
Berisha et al.

(10) Patent No.: US 10,796,715 B1
(45) Date of Patent: Oct. 6, 2020

(54) SPEECH ANALYSIS ALGORITHMIC SYSTEM AND METHOD FOR OBJECTIVE EVALUATION AND/OR DISEASE DETECTION

(71) Applicant: Arizona Board of Regents on behalf of Arizona State University, Scottsdale, AZ (US)

(72) Inventors: Visar Berisha, Tempe, AZ (US); Ming Tu, Tempe, AZ (US); Alan Wisler, Plano, TX (US); Julie Liss, Scottsdale, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 502 days.

(21) Appl. No.: 15/693,699

(22) Filed: Sep. 1, 2017

Related U.S. Application Data

(60) Provisional application No. 62/382,494, filed on Sep. 1, 2016.

(51) Int. Cl.
*G10L 25/66* (2013.01)
*A61B 5/00* (2006.01)
(Continued)

(52) U.S. Cl.
CPC .......... *G10L 25/66* (2013.01); *A61B 5/4803* (2013.01); *A61B 5/48* (2013.01); *A61B 5/7264* (2013.01);
(Continued)

(58) Field of Classification Search
CPC ....... A61B 5/4803; A61B 5/7267; A61B 5/48; A61B 5/7264; G10L 2015/022;
(Continued)

(56) References Cited

U.S. PATENT DOCUMENTS 5,774,846 A * 6/1998 Morii ..................... G10L 19/06
704/202
6,446,038 B1 * 9/2002 Bayya .................... G10L 25/69
704/231
(Continued)

FOREIGN PATENT DOCUMENTS

WO 2006109268 A1 10/2006
WO 2007135605 A1 11/2007

OTHER PUBLICATIONS

Steven Greenberg and Takayuki Arai, The Relation Between Speech Intelligibility and the Complex Modulation Spectrum, 2001, International Computer Science Institute (Year: 2001).*
(Continued)

*Primary Examiner* — Sean P Dougherty
(74) *Attorney, Agent, or Firm* — Withrow & Terranova, P.L.L.C.

(57) ABSTRACT

Systems and methods use patient speech samples as inputs, use subjective multi-point ratings by speech-language pathologists of multiple perceptual dimensions of patient speech samples as further inputs, and extract laboratory-implemented features from the patient speech samples. A predictive software model learns the relationship between speech acoustics and the subjective ratings of such speech obtained from speech-language pathologists, and is configured to apply this information to evaluate new speech samples. Outputs may include objective evaluation of the plurality of perceptual dimensions for new speech samples and/or evaluation of disease onset, disease progression, or disease treatment efficacy for a condition involving dysarthria as a symptom, utilizing the new speech samples.

20 Claims, 14 Drawing Sheets

(51) Int. Cl.
| | | |
|---|---|---|
| *G10L 25/51* | (2013.01) | |
| *G10L 25/78* | (2013.01) | |
| *G10L 15/02* | (2006.01) | |
| *G10L 25/90* | (2013.01) | |
| *G10L 25/60* | (2013.01) | |
| *G10L 15/16* | (2006.01) | |
| *G10L 15/22* | (2006.01) | |

(52) U.S. Cl.
CPC .............. *A61B 5/7267* (2013.01); *G10L 15/02* (2013.01); *G10L 15/16* (2013.01); *G10L 15/22* (2013.01); *G10L 25/51* (2013.01); *G10L 25/60* (2013.01); *G10L 25/78* (2013.01); *G10L 25/90* (2013.01); *G10L 2015/022* (2013.01); *G10L 2015/025* (2013.01); *G10L 2015/027* (2013.01)

(58) Field of Classification Search
CPC ......... G10L 2015/025; G10L 2015/027; G10L 15/22; G10L 25/60; G10L 25/90; G10L 15/16; G10L 25/78; G10L 25/51; G10L 15/02; G10L 25/66
See application file for complete search history.

(56) References Cited

U.S. PATENT DOCUMENTS

| | | | | |
|---|---|---|---|---|
| 2003/0078768 | A1* | 4/2003 | Silverman | ............... G10L 17/26 704/206 |
| 2007/0276270 | A1* | 11/2007 | Tran | ..................... A61B 5/0022 600/508 |
| 2009/0023422 | A1* | 1/2009 | MacInnis | ................ G06F 16/84 455/411 |
| 2013/0345524 | A1 | 12/2013 | Meyer et al. | |
| 2014/0073993 | A1* | 3/2014 | Poellabauer | ............. A61B 7/00 600/586 |
| 2015/0154980 | A1 | 6/2015 | Khan et al. | |
| 2015/0265205 | A1* | 9/2015 | Rosenbek | ............ A61B 5/4082 600/586 |
| 2015/0380009 | A1* | 12/2015 | Chang | ..................... G10L 25/06 704/263 |

OTHER PUBLICATIONS

Lingyun Gu, John G. Harris, Rahul Shrivastav, Christine Sapienza, Disordered Speech Evaluation Using Objective Quality Measures, 2005, Department of Electrical and Computer Engineering (Year: 2005).*

Visar Berisha, Julie Liss1 Steven Sandoval, Rene Utianski, and Andreas Spanias, Modeling Pathological Speech Perception From Data With Similarity Labels, 2014 IEEE International Conference on Acoustic, Speech and Signal Processing (Year: 2014).*

Tiago H. Falk, Quantifying Perturbations in Temporal Dynamics for Automated Assessment of Spastic Dysarthric Speech Intelligibility, 2011, IEEE pp. 4480-4483 (Year: 2011).*

Visar Berisha, Steven Sandoval, Rene Utianski, Julie Liss, and Andreas Spanias, Selecting Disorder-Specific Features for Speech Pathology Fingerprinting, 2013, Arizona State University (Year: 2013).*

Visar Berisha, Rene Utianski, and Julie Liss, Towards a Clinical Tool for Automatic Intelligibility Assessment, 2013, Department of Speech and Hearing Science, Arizona State University (Year: 2013).*

Author Unknown, "Feature Selection, Sparsity, Regression Regularization," Lecture notes for Machine Learning course held at the College of Computer and Information Science of Northeastern University, Accessed Aug. 28, 2017, 7 pages.

Bunton, K., et al. "Listener Agreement for Auditory-Perceptual Ratings of Dysarthria," Journal of Speech, Language, and Hearing Research, vol. 50, Dec. 2007, pp. 1481-1495.

Mashima, P. A., et al., "Overview of Telehealth Activities in Speech-Language Pathology," Telemedicine and e-Health, vol. 14, No. 10, Dec. 2008, pp. 1101-1117.

Hastie, T., et al., "Statistical Learning with Sparsity: The Lasso and Generalizations," Monographs on Statistics and Applied Probability 143, CRC Press: Taylor & Francis Group, Corrected Dec. 19, 2016, 362 pages.

* cited by examiner

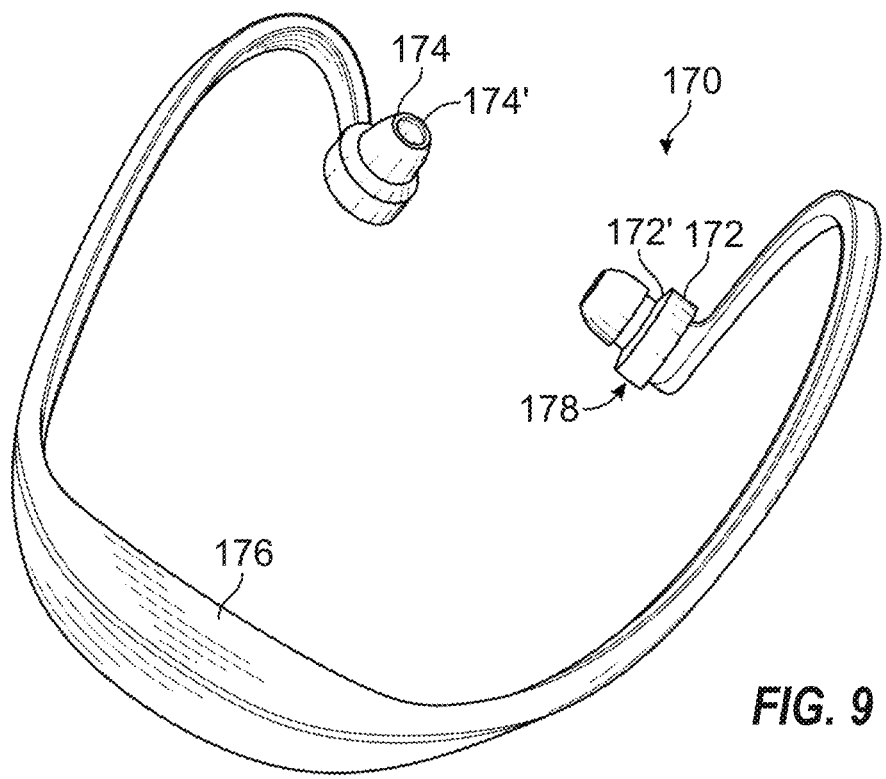
FIG. 9
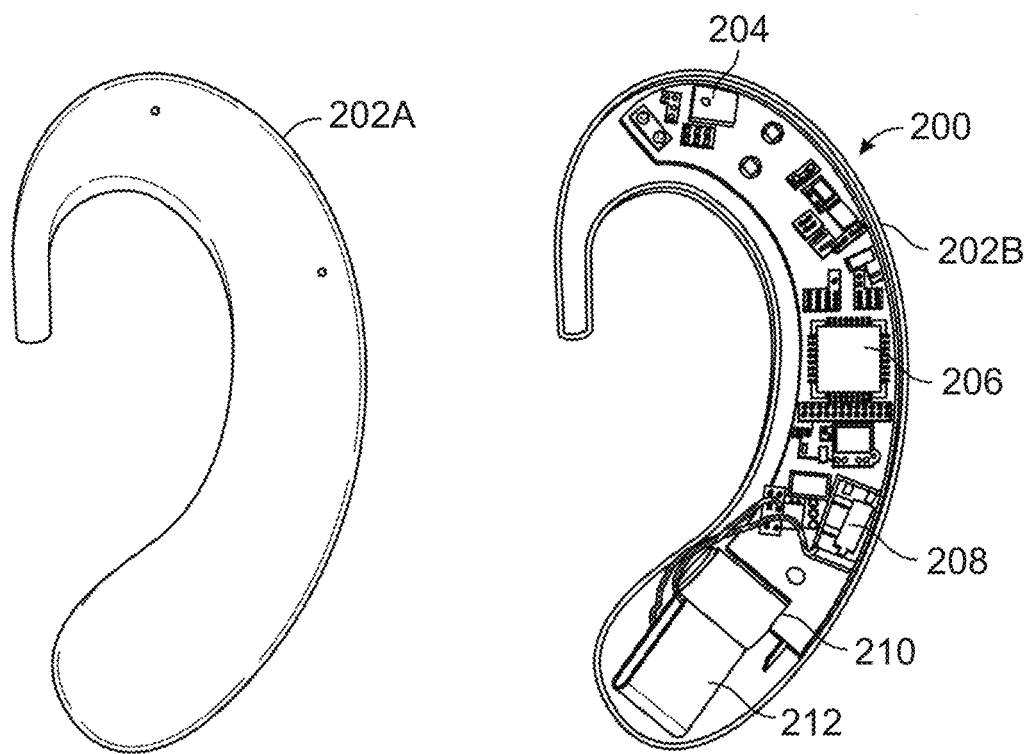
FIG. 10A
FIG. 10B

SPEECH ANALYSIS ALGORITHMIC SYSTEM AND METHOD FOR OBJECTIVE EVALUATION AND/OR DISEASE DETECTION

CROSS-REFERENCE TO RELATED APPLICATION(S)

This application claims the benefit of U.S. Provisional Patent Application No. 62/382,494 filed on Sep. 1, 2016, the disclosure of which is hereby incorporated by reference herein in its entirety.

GOVERNMENT RIGHTS IN INVENTION

This invention was made with government support under R21 DC012558 awarded by the National Institutes of Health. The government has certain rights in the invention.

TECHNICAL FIELD

This disclosure relates to systems and methods for speech evaluation and/or analysis, and in certain aspects to evaluation of disease onset, disease progression, disease treatment efficacy and/or need for therapeutic intervention for a condition including dysarthria as a symptom.

BACKGROUND

A speech-language pathologist (SLP) works with adults and children having difficulty with speech or processing language properly. Their patients may have problems related to motor and physical skills, as well as cognitive issues affecting the ability to express language.

One type of motor speech disorder is dysarthria, which is characterized by poor articulation of phonemes—a condition in which muscles that produce speech experience problems that make it difficult for a speaker to pronounce words. Neurological injury due to damage in the central or peripheral nervous system may result in weakness, paralysis, or a lack of coordination of motor components of the motor-speech system, producing dysarthria. Various potential causes of dysarthria broadly include toxic conditions, metabolic conditions, degenerative diseases, traumatic brain injury, or thrombotic or embolic stroke. Specific examples of toxic and metabolic conditions include Wilson's disease, hypoxic encephalopathy such as occurs in drowning, and central pontine myelinolysis. Specific examples of other conditions that may lead to dysarthria include brain tumors, cerebral palsy, Guillain-Barré syndrome, hypothermia, Lyme disease, intercranial hypertension, and Tay-Sachs (including late onset Tay-Sachs or LOTS) disease.

Dysarthria can affect one or more of the respiration, phonation, resonance, prosody, and articulation speech subsystems, thereby leading to impaired intelligibility, audibility, naturalness, and efficiency of spoken communication. Dysarthria can progress to a total loss of speech, referred to as anarthria.

Dysarthrias are classified in multiple ways based on the presentation of symptoms. Specific dysarthrias include spastic (resulting from bilateral damage to the upper motor neuron), flaccid (resulting from bilateral or unilateral damage to the lower motor neuron), ataxic (resulting from damage to the cerebellum), unilateral upper motor neuron (presenting milder symptoms than bilateral upper motor neuron damage), hyperkinetic and hypokinetic (resulting from damage to parts of the basal ganglia, such as in Huntington's disease or Parkinsonism), and mixed dysarthrias (in which symptoms of more than one type of dysarthria are present). Individuals with dysarthria may experience challenges in one or more of timing, vocal quality, pitch, volume, breath control, speed, strength, steadiness, range, and tone.

Speech-language pathologists are involved in diagnosis of dysarthria and treatment of articulation problems resulting from dysarthria.

Speech-language pathologists typically use perceptual assessment to make clinical diagnoses, severity judgments, and management decisions, and to judge disease progression. Clinical assessments are predominantly conducted through subjective tests performed by speech-language pathologists (e.g. making subjective estimations of the amount of speech that can be understood, number of words correctly understood in a standard test battery, etc.). Perceptual judgments are easy to render and have strong face validity for characterizing speech deficits. Subjective tests, however, can be inconsistent and costly, often are not repeatable, and subjective judgments may be highly vulnerable to bias. In particular, repeated exposure to the same test subject (e.g., patient) over time can influence the assessment ratings generated by a speech-language pathologist. As such, there is an inherent ambiguity about whether the patient's intelligibility is confounded with increased familiarity with the patient's speech, as both may affect subjective assessment by the speech-language pathologist.

Existing objective measures in speech and language clinics focus on measuring aspects of speech signals that are not interpretable in clinical settings. Examples of such objective measures include instruments that measure pitch, formants, energy, and other similar metrics.

A need exists in the art to provide a platform to bridge the subjective-objective divide by combining the face validity of perceptual assessment with a system providing reliable objective outcome measures so as to affect diagnosis of dysarthrias and the standard of care for motor speech assessment.

SUMMARY

The present disclosure involves creation and use of novel speech analysis algorithms that offer an objective measure of the subjective assessments typically performed by speech-language pathologists. A principal objective is to offer a platform to sensitively assess therapeutic need, disease onset, disease progression, and treatment efficacy with unbiased, perception-calibrated metrics. Clinically meaningful speech quantification will for the first time provide valid and reliable outcome measures, as is necessary for day-to-day clinical decision-making, and for the evaluation of efficacy of therapeutic interventions. Systems and methods disclosed herein have the potential to radically alter the standard of care for motor speech assessment, and to transform speech disorder evaluation by enabling integration into existing telehealth platforms for on-the-spot objective outcome measures.

Systems and methods disclosed herein use patient speech samples as inputs, use subjective ratings by speech-language pathologists of patient speech samples as further inputs, and extract laboratory-implemented features from the patient speech samples. The subjective ratings may evaluate of the speech on a multi-point (e.g., 7-point) scale for five commonly assessed perceptual dimensions, namely: nasality, prosody, articulatory precision, vocal quality, and severity. A predictive software model learns the relationship between speech acoustics (embodied in the laboratory-implemented features) and the subjective ratings of the same speech obtained from speech-language pathologists, and is configured to apply this information to evaluate new speech samples. Signal processing capabilities and machine learning algorithms may be utilized to continually refine the model with increased input, to permit algorithms of the predictive software model to become more refined with each iteration. Thus, the output of the predictive software model is immediately clinically transparent, and does not require any norms or references for comparison. Systems and methods disclosed herein have the potential to transform speech disorder evaluation, by permitting integration into existing telehealth platforms to provide on-the-spot objective outcome measures.

In one aspect, the present disclosure relates to a method for evaluating speech in a system involving processor circuitry, the method comprising: selecting a subset of a plurality of laboratory-implemented features from a data matrix that includes (i) the plurality of laboratory-implemented features, wherein said plurality of laboratory-implemented features is extracted from a plurality of patient speech samples, and (ii) a plurality of subjective expert ratings corresponding to the plurality of patient speech samples and involving evaluations on a multi-point scale for a plurality of perceptual dimensions including two or more of nasality, prosody, articulatory precision, vocal quality, and severity; wherein the subset of the plurality of laboratory-implemented features is relevant for predicting the plurality of perceptual dimensions; and wherein the plurality of laboratory-implemented features comprises an envelope modulation spectrum, a long-term average spectrum, spatio-temporal features, and dysphonia features; and utilizing the subset of the plurality of laboratory-implemented features to generate and/or update a predictive software model configured to receive at least one additional patient speech sample and to perform at least one of the following items (a) or (b): (a) generating an objective evaluation of the plurality of perceptual dimensions utilizing the at least one additional patient speech sample; or (b) evaluating at least one of disease onset, disease progression, or disease treatment efficacy for a condition involving dysarthria as a symptom, utilizing the at least one additional patient speech sample.

In certain embodiments, the method further comprises electronically receiving the plurality of patient speech samples and the plurality of subjective expert ratings; and extracting the plurality of laboratory-implemented features from the plurality of patient speech samples for inclusion in the data matrix.

In certain embodiments, the method further comprises electronically receiving the at least one additional patient speech sample; and generating an objective evaluation of the plurality of perceptual dimensions utilizing the at least one additional patient speech sample.

In certain embodiments, the method further comprises electronically receiving the at least one additional patient speech sample; and evaluating at least one of disease onset, disease progression, or disease treatment efficacy for a condition involving dysarthria as a symptom, utilizing the at least one additional patient speech sample.

In certain embodiments, the method further comprises prompting at least one patient to read displayed text prior to, or concurrently with, the electronic receiving of the at least one additional patient speech sample. In certain embodiments, the method further comprises providing user-perceptible feedback to the at least one patient while the at least one patient reads the displayed text, to alert the at least one patient to attainment of one or more conditions indicative of a speech problem. In certain embodiments, the user-perceptible feedback comprises tactile feedback.

In certain embodiments, the plurality of perceptual dimensions includes each of nasality, prosody, articulatory precision, vocal quality, and severity.

In certain embodiments, the selecting of the subset of the plurality of laboratory-implemented features comprises use of lasso or $\ell_1$-regularized regression.

In certain embodiments, the selecting of the subset of the plurality of laboratory-implemented features comprises use of cross-validation and sparsity-based feature selection.

In certain embodiments, the selecting of the subset of the plurality of laboratory-implemented features further comprises centering data of the subset. In certain embodiments, the selecting of the subset of the plurality of laboratory-implemented features further comprises reducing the subset of the plurality of laboratory-implemented features to less than about 40 for each dimension of the plurality of perceptual dimensions.

In another aspect, the disclosure relates to a computer program comprising instructions which, when executed by processor circuitry including at least one processor, cause the at least one processor to carry out the method as disclosed herein.

In another aspect, the disclosure relates to a system for evaluating speech, the system comprising: at least one memory configured to store a data matrix including (i) a plurality of laboratory-implemented features extracted from a plurality of patient speech samples and (ii) a plurality of subjective expert ratings corresponding to the plurality of patient speech samples and involving evaluations on a multi-point scale for a plurality of perceptual dimensions including two or more of nasality, prosody, articulatory precision, vocal quality, and severity; wherein the plurality of laboratory-implemented features comprises an envelope modulation spectrum, a long-term average spectrum, spatio-temporal features, and dysphonia features; and processor circuitry configured to (A) select a subset of the plurality of laboratory-implemented features that is relevant for predicting the plurality of perceptual dimensions, and (B) utilize the subset of the plurality of laboratory-implemented features to generate and/or update a predictive software model that is configured to receive at least one additional patient speech sample and is configured to perform at least one of the following items (a) or (b): (a) generate an objective evaluation of the plurality of perceptual dimensions utilizing the at least one additional patient speech sample; or (b) evaluate at least one of disease onset, disease progression, or disease treatment efficacy for a condition involving dysarthria as a symptom, utilizing the at least one additional patient speech sample.

In certain embodiments, the processor circuitry is further configured to extract the plurality of laboratory-implemented features from the plurality of patient speech samples for inclusion in the data matrix.

In certain embodiments, the plurality of perceptual dimensions includes each of nasality, prosody, articulatory precision, vocal quality, and severity.

In certain embodiments, the selecting of the subset of the plurality of laboratory-implemented features comprises use of lasso or $\ell_1$-regularized regression.

In certain embodiments, the processor circuitry is configured to select the subset of the plurality of laboratory-implemented features utilizing cross-validation and sparsity-based feature selection.

In certain embodiments, the system further comprises an audio input configured to electronically receive the at least one additional patient speech sample. In certain embodiments, the system further comprises a display generator configured to provide a displayable signal prompting at least one patient to read displayed text prior to, or concurrently with, electronic reception of the at least one additional patient speech sample.

In another aspect, the disclosure relates to a non-transitory computer readable medium storing software instructions that, when executed by one or more processors of a speech evaluation system, cause the speech evaluation system to: select a subset of a plurality of laboratory-implemented features from a data matrix that includes (i) the plurality of laboratory-implemented features, wherein said plurality of laboratory-implemented features is extracted from a plurality of patient speech samples, and (ii) a plurality of subjective expert ratings corresponding to the plurality of patient speech samples and involving evaluations on a multi-point scale for a plurality of perceptual dimensions including two or more of nasality, prosody, articulatory precision, vocal quality, and severity; wherein the subset of the plurality of laboratory-implemented features is relevant for predicting the plurality of perceptual dimensions; and wherein the plurality of laboratory-implemented features comprises an envelope modulation spectrum, a long-term average spectrum, spatio-temporal features, and dysphonia features; and utilize the subset of the plurality of laboratory-implemented features to generate and/or update a predictive model configured to receive at least one additional patient speech sample and to perform at least one of the following items (a) or (b): (a) generate an objective evaluation of the plurality of perceptual dimensions utilizing the at least one additional patient speech sample; or (b) evaluate at least one of disease onset, disease progression, or disease treatment efficacy for a condition involving dysarthria as a symptom, utilizing the at least one additional patient speech sample.

In certain embodiments, the software instructions are further configured to cause the speech evaluation system to: electronically receive the plurality of patient speech samples and the plurality of subjective expert ratings; and extract the plurality of laboratory-implemented features from the plurality of patient speech samples for inclusion in the data matrix.

In certain embodiments, the software instructions are further configured to cause the speech evaluation system to: electronically receive the at least one additional patient speech sample; and generate an objective evaluation of the plurality of perceptual dimensions utilizing the at least one additional patient speech sample.

In certain embodiments, the software instructions are further configured to cause the speech evaluation system to: electronically receive the at least one additional patient speech sample; and evaluate at least one of disease onset, disease progression, or disease treatment efficacy for a condition involving dysarthria as a symptom, utilizing the at least one additional patient speech sample.

In certain embodiments, the software instructions are further configured to cause the speech evaluation system to prompt at least one patient to read displayed text prior to, or concurrently with, the electronic receiving of the at least one additional patient speech sample.

In certain embodiments, the software instructions are further configured to cause the speech evaluation system to provide user-perceptible feedback to at least one patient while the at least one patient reads the displayed text, to alert the at least one patient to attainment of one or more conditions indicative of a speech problem. In certain embodiments, the user-perceptible feedback comprises tactile feedback.

In certain embodiments, the plurality of perceptual dimensions includes each of nasality, prosody, articulatory precision, vocal quality, and severity.

In certain embodiments, the selecting of the subset of the plurality of laboratory-implemented features comprises use of lasso or $\ell_1$-regularized regression.

In certain embodiments, the selecting of the subset of the plurality of laboratory-implemented features comprises use of cross-validation and sparsity-based feature selection.

In yet another aspect, the disclosure relates to a system for evaluating speech, the system comprising: at least one memory configured to store a plurality of patient speech samples and a plurality of subjective expert ratings corresponding to the plurality of patient speech samples, wherein each subjective expert rating of the plurality of subjective expert ratings includes evaluation on a multi-point scale for a plurality of perceptual dimensions including nasality, prosody, articulatory precision, vocal quality, and severity; and processor circuitry configured to (A) extract a plurality of laboratory-implemented features from the plurality of patient speech samples to generate a data matrix, wherein the plurality of laboratory-implemented features comprises an envelope modulation spectrum, a long-term average spectrum, spatio-temporal features, and dysphonia features; (B) select a subset of the plurality of laboratory-implemented features relevant for predicting the plurality of perceptual dimensions; and (C) generate and/or update a predictive software model that is configured to receive at least one additional patient speech sample and to perform at least one of (i) generating an objective evaluation of the plurality of perceptual dimensions utilizing the at least one additional patient speech sample or (ii) evaluating at least one of disease onset, disease progression, or disease treatment efficacy for a condition involving dysarthria as a symptom, utilizing the at least one additional patient speech sample.

In certain embodiments, the system further comprises one or more signal inputs configured to (a) electronically receive the plurality of patient speech samples, (b) electronically receive the plurality of subjective expert ratings corresponding to the plurality of patient speech samples, and (c) electronically receive the at least one additional patient speech sample.

In another aspect, the disclosure relates to a method for evaluating speech in a system involving processor circuitry, the method comprising: electronically receiving (i) a plurality of patient speech samples and (ii) a plurality of subjective expert ratings corresponding to the plurality of patient speech samples, wherein each subjective expert rating of the plurality of subjective expert ratings includes evaluation on a multi-point scale for a plurality of perceptual dimensions including nasality, prosody, articulatory precision, vocal quality, and severity; extracting a plurality of laboratory-implemented features from the plurality of patient speech samples to generate a data matrix, wherein the plurality of laboratory-implemented features comprises an envelope modulation spectrum, a long-term average spectrum, spatio-temporal features, and dysphonia features; selecting a subset of the plurality of laboratory-implemented features relevant for predicting the plurality of perceptual dimensions; and utilizing the subset of the plurality of laboratory-implemented features to generate and/or update a predictive software model that is configured to receive at least one additional patient speech sample and perform at least one of (a) generating an objective evaluation of the plurality of perceptual dimensions utilizing the at least one additional patient speech sample or (b) evaluating at least one of disease onset, disease progression, or disease treatment efficacy for a condition involving dysarthria as a symptom, utilizing the at least one additional patient speech sample.

In another aspect, the disclosure relates to a computer program comprising instructions which, when executed by processor circuitry including at least one processor, cause the at least one processor to carry out the method as disclosed herein.

In certain aspects, any of the preceding aspects or other features disclosed here may be combined for additional advantage.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

FIG. 7A illustrates a first graphical user interface screen for eliciting a patient to provide a speech sample for acquisition by a speech evaluation system according to one embodiment of the present disclosure.

FIG. 8 illustrates superimposed third and fourth graphical user interface screens for a speech evaluation system, according to one embodiment of the present disclosure.

FIG. 9 is a perspective view illustration of a behind-the-neck headset device useable with a speech evaluation system, according to one embodiment of the present disclosure.

FIGS. 10A and 10B provide side elevation views of two halves of a behind-the-ear device incorporating electronic circuitry useable for speech sample acquisition and/or processing and useable with a speech evaluation system, according to one embodiment of the present disclosure.

DETAILED DESCRIPTION

Figure 1:
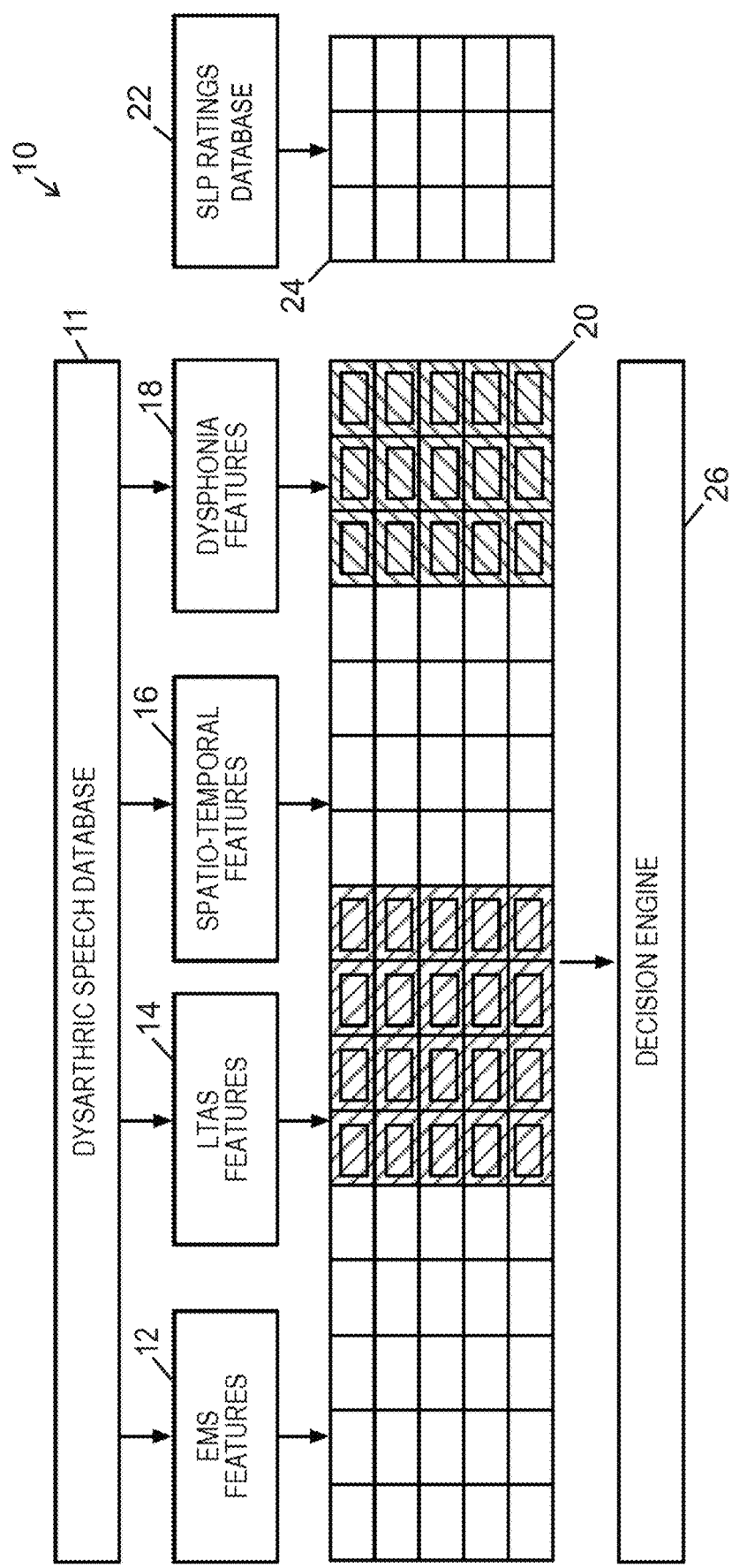
FIG. 1 is a high-level schematic diagram of operation of an algorithm for extracting a set of laboratory-implemented features that capture irregularities in the speech of a specific patient, and that are supplied to a decision engine (or other processor circuitry) that may further receive subjective expert ratings for a plurality of perceptual dimensions of patient speech, according to one embodiment of the present disclosure.

The embodiments set forth herein represent the necessary information to enable those skilled in the art to practice the embodiments and illustrate the best mode of practicing the embodiments. Upon reading the description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

In certain aspects, the present disclosure relates to a method for evaluating speech, a system for evaluating speech, a non-transitory computer readable medium storing software instructions, and a computer program including instructions for causing a processor to carry out a method.

In certain embodiments, a data matrix may be generated, said data matrix incorporating processed speech samples and speech-language pathologist ratings corresponding to the speech samples. Processing of the speech samples includes extraction of a plurality of laboratory-implemented features (e.g., an envelope modulation spectrum, a long-term average spectrum, spatio-temporal features, and dysphonia features). The speech-language pathologist ratings include subjective multi-point ratings of commonly assessed perceptual dimensions (e.g., two, three, four, or all five of nasality, prosody, articulatory precision, vocal quality, and severity). A subset of the plurality of laboratory-implemented features that is relevant for predicting a plurality of perceptual dimensions, and that simplifies computation by reducing multi-collinearity, is selected. The subset includes a unique set of laboratory-implemented features per dimension, and data therein may be centered and reduced to a manageable number of features (e.g., no greater than about 50, about 40, about 30, or about 25 features per perceptual dimension). The resulting feature set may be employed as an input to a predictive software model (e.g., an objective evaluation linear model) that predicts objective ratings from the down-selected and centered feature set representative of speech acoustics. The predictive software model captures the relationship between speech acoustics and subjective ratings. Cross-validation (or more preferably a combination of cross-validation and sparsity based-feature selection) may be used to generate and/or update (e.g., calibrate) a predictive software model that is configured to receive at least one additional patient speech sample and perform at least one of (a) generating an objective evaluation of the plurality of perceptual dimensions utilizing the at least one additional patient speech sample or (b) evaluating at least one of disease onset, disease progression, or disease treatment efficacy for a condition involving dysarthria as a symptom, utilizing the at least one additional patient speech sample. In certain embodiments, the objective evaluation of the plurality of perceptual dimensions includes a multi-point evaluation spanning all five dimensions outlined above.

The subject matter described herein may be implemented in hardware, software, firmware, or any combination thereof. As such, the terms 'function" or "module" may be used herein to refer to hardware, software, and/or firmware for implementing the feature being described.

In one exemplary implementation, the subject matter described herein may be implemented using a computer readable medium having stored thereon executable instructions that, when executed by the processor of a computer, direct the computer to perform steps. Exemplary computer readable media suitable for implementing the subject matter described herein include disk memory devices (e.g., a compact disc (CD) or a digital video disc (DVD)), chip memory devices (e.g., a USB drive or memory card), programmable logic devices, application specific integrated circuits, network storage devices, and other non-transitory storage media. In one implementation, the computer readable medium may include a memory accessible by a processor of a computer or other like device. The memory may include instructions executable by the processor for implementing any of the methods described herein. In addition, a computer readable medium that implements the subject matter described herein may be located on a single device or computing platform, or may be distributed across multiple physical devices and/or computing platforms. An exemplary processor (also referred to as a processor circuit or processor circuitry) may comprise microprocessor(s), Central Processing Unit(s) (CPU(s)), Application Specific Integrated Circuit(s) (ASIC(s)), Field Programmable Gate Array(s) (FPGA(s)), or the like.

An initial step in building a predictive software model or decision engine is formation of a data matrix. For all speech samples in a database, a series of laboratory-implemented features are extracted. These laboratory-implemented features include two or more (or more preferably all of) the envelope modulation spectrum, the long-term average spectrum, spatio-temporal features, and dysphonia features. Such features are described hereinafter.

The envelope modulation spectrum (EMS) is a representation of slow-amplitude modulations in a signal and the distribution of energy in amplitude fluctuations across designated frequencies, collapsed over time. EMS has been shown to be a useful indicator of atypical rhythm patterns in pathological speech.

Each speech segment in a preexisting pathological speech database, x(t), is filtered into 7 octave bands with center frequencies of 125, 250, 500, 1000, 2000, 4000, and 8000 Hz. $h_i(t)$ denotes the filter associated with the $i^{th}$ octave. The filtered signal, $x_i(t)$, is then denoted by:

$$x_i(t)=h_i(t)*x(t)$$

The envelope in the $i^{th}$ octave, denoted by $e_i(t)$, is extracted by:

$$e_i(t)=h_{LPF}(t)*H(x(t))$$

where H(.) is the Hilbert transform and $h_{LPF}(t)$ is the impulse response of a 20 Hz low-pass filter.

Once the amplitude envelope of the signal is obtained, the low-frequency variation in the amplitude levels of the signal can be examined. Fourier analysis quantifies the temporal regularities of the signal. Six EMS metrics are then computed from the resulting envelope spectrum for each of the 7 octave bands, $x_i(t)$, and the full signal, x(t): 1) Peak frequency, 2) Peak amplitude, 3) Energy in the spectrum from 3-6 Hz, 4) Energy in the spectrum from 0-4 Hz, 5) Energy in the spectrum from 4-10 Hz, and 6) Energy ratio between 0-4 Hz band and 4-10 Hz band.

The long-term average spectrum (LTAS) captures atypical average spectral information in the signal. Nasality, breathiness, and atypical loudness variation, which are common causes of intelligibility deficits in dysarthric speech, present as atypical distributions of energy across the spectrum; LTAS measures these cues in each octave. For each of the 7 octave bands, $x_i(t)$, and the full signal, x(t), the following are extracted: 1) average normalized root mean square (RMS) energy, 2) RMS energy standard deviation, 3) RMS energy range, and 4) pairwise variability of RMS energy between ensuing 20 ms frames.

The spatio-temporal features capture the evolution of vocal tract shape and dynamics in different time scales via auto- and cross-correlation analysis of formant tracks and mel-frequency cepstral coefficients (MFCC).

The dysphonia features capture atypical vocal quality through the analysis of pitch changes and pitch amplitude changes over time.

The data matrix generated by processing the speech samples and extracting the laboratory-implemented features results in high dimensional data. Regression in high dimensional space is notoriously difficult: dimensionality requires exponential growth in the number of exemplars as the intrinsic dimension of the data increases. Thus, a processor-implemented routine is constructed and implemented to select only a relevant subset of these features, through a combination of cross-validation and sparsity-based feature selection (e.g., involving lasso or $\ell_1$-regularized regression). Restated, subsets of acoustic metrics that map to perceptual ratings are identified. The selection criterion aims to (1) identify a subset of laboratory-implemented features that are relevant for predicting each of the five perceptual dimensions (nasality, prosody, articulatory precision, vocal quality, and severity) and (2) reduce the multi-collinearity problem, thereby enabling practical computation. This subset selection results in a unique set of features per perceptual dimension. Following this down-selection, principal components analysis may be used to center the data and further reduce the feature set to a manageable number (e.g., no greater than about 50, about 40, about 30, or about 25) for each dimension. This new centered feature set may advantageously be used as an input to the predictive software model, to permit objective evaluation of the plurality of perceptual dimensions (nasality, prosody, articulatory precision, vocal quality, and severity) from an additional patient speech sample. Automated acoustic measures disclosed herein are specifically designed to address challenges of dysarthric speech analysis.

For each perceptual dimension, the predictive software model (e.g., an objective evaluation linear model) predicts an objective rating (optionally expressed on a multi-point such as a 7-point scale) from the down-selected and centered speech acoustics. In certain embodiments, cross-validation is used to train the predictive software model. Cross-validation involves partitioning the data matrix into complementary subsets, learning the parameters of the decision engine on one subset (training speakers), and validating on the remaining subset (testing speakers). The error on the (held out) test data set is used to assess the predictive power of the predictive software model. A framework for generating a predictive software model utilizing cross-validation and sparsity-based feature selection (e.g., lasso or $\ell_1$-regularized regression) follows.

In general, a sparse statistical model is one in which only a relatively small number of parameters (or predictors) play an important role.

A leading example of a method that employs sparsity is linear regression, in which N observations of an outcome variable $y_i$ and p associated predictor variables (or features) $x_i = (x_{i1}, \ldots x_{ip})^T$ are observed. The goal is to predict an outcome from the predictors—both for actual prediction of future data and also to discover which predictors play an important role. A linear regression model assumes that:

$$y_i = \beta_0 + \sum_{j=1}^{p} x_{ij}\beta_j + e_i,$$

where $\beta_0$ and $\beta=(\beta_1, \beta_2, \ldots \beta_p)$ are unknown parameters and $e_i$ is an error term. The method of least-squares provides estimates of the parameters by minimization of the least-squares objective function:

$$\underset{\beta_0,\beta}{\text{minimize}} \sum_{i=1}^{N}\left(y_i - \beta_0 - \sum_{j=1}^{p} x_{ij}\beta_j\right)^2$$

One limitation with the least-squares method is that interpretation of the final model is challenging if p is large. If p>N, then the least-squares estimates are not unique. In such a situation, an infinite set of solutions will make the objective function equal to zero, and these solutions tend to overfit the data as well.

In view of the limitations of the least-squares method, there is a need to constrain, or regularize, the estimation process. Such need is addressed by "lasso" or "$\ell_1$-regularized" regression, in which parameters are estimated by solving the problem:

$$\underset{\beta_0,\beta}{\text{minimize}} \sum_{i=1}^{N}\left(y_i - \beta_0 - \sum_{j=1}^{p} x_{ij}\beta_j\right)^2 \text{ subject to } \|\beta\|_1 \leq t$$

where $\|\beta\|_1 = \sum_{i=1}^{p}|\beta_j|$ is the $\ell_1$ norm of $\beta$, where t is a user-specified parameter. The parameter t can be considered a budget on the total $\ell_1$ norm of the parameter vector, and the lasso finds the best fit within this budget. If the budget t is small enough, the lasso yields sparse solution vectors, having only some coordinates that are nonzero. The bound t in the lasso criterion is a kind of budget, in that it limits the sum of the absolute values of the parameter estimates, and controls the complexity of the model. In particular, larger values of t free up more parameters and allow the model to adapt more closely to the training data. Conversely, smaller values of t restrict the parameters more, leading to sparser, more interpretable models that fit the data less closely. The $\ell_1$-norm represents the smallest value that yields a convex problem. Convexity simplifies the computation, and allows for scalable algorithms that can handle problems with a multitude of parameters.

The advantages of sparsity are therefore interpretation of the fitted model and computational convenience. But in recent years, a third advantage has emerged from mathematical analysis of this area, with such advantage being termed the "bet on sparsity" principle, namely: Use a procedure that does well in sparse problems, since no procedure does well in dense problems.

The lasso estimator for linear regression is a method that combines the least-squares loss with an $\ell_1$-constraint (or bound) on the sum of the absolute values of the coefficients. Relative to the least-squares solution, this constraint has the effect of shrinking the coefficients, and even setting some to zero. In this way, it provides an automatic method for performing model selection in linear regression. Moreover, unlike some other criteria for model selection, the resulting optimization problem is convex, and can be solved efficiently for large problems.

Given a collection of N predictor-response pairs $\{(x_i,y_i)\}_{i=1}^{N}$, the lasso finds the solution $(\widehat{\beta_o}, \beta)$ to the optimization problem:

$$\underset{\beta_0,\beta}{\text{minimize}} \left\{\frac{1}{2N}\sum_{i=1}^{N}\left(y_i - \beta_0 - \sum_{j=1}^{p} x_{ij}\beta_j\right)^2\right\} \text{ subject to } \sum_{j=1}^{p}|\beta_j| \leq t.$$

The preceding ("subject to . . . ") constraint can be written more compactly as the $\ell_1$-norm constraint $\|\beta\|_1 \leq t$. Furthermore, the lasso optimization problem outlined above is often represented using matrix-vector notation. If $y=(y_1, \ldots, y_N)$ denotes the N-vector of responses and X is an N×p matrix with $x_i \in R^p$ in its $i^{th}$ row, then the lasso optimization problem can be re-expressed as:

$$\underset{\beta_0,\beta}{\text{minimize}} \left\{\frac{1}{2N}\|y - \beta_0 1 - X\beta\|_2^2\right\} \text{ subject to } \|\beta\|_1 \leq t,$$

where 1 is the vector of N ones, and $\|.\|_2$ denotes the usual Euclidean norm on vectors.

The predictors X may be standardized so that each column is centered according to:

$$\left(\frac{1}{N}\sum_{i=1}^{N} x_{ij} = 0\right)$$

and has unit variance:

$$\left(\frac{1}{N}\sum_{i=1}^{N} x_{ij}^2 = 1\right).$$

Without standardization, the lasso solutions would depend on the units (e.g., pounds vs. kilograms, or meters vs. feet) used to measure the predictors, but standardization would not be necessary if all features were measured in the same units. For convenience, the outcome values $y_i$ may be centered (such that the intercept term $B_o$ can be omitted in the lasso optimization), with such centering meaning that:

$$\frac{1}{N}\sum_{i=1}^{N} y_i = 0.$$

It is often convenient to rewrite the lasso problem in the so-called Lagrangian form:

$$\underset{\beta \in \mathbb{R}^p}{\text{minimize}}\left\{\frac{1}{2N}\|y - X\beta\|_2^2 + \lambda\|\beta\|_1\right\},$$

for some $\lambda \geq 0$. By Lagrangian duality, there is a one-to-one correspondence between the constrained problem (i.e., minimization of $\beta_o$, $\beta$) and the Lagrangian form. That is, for each value of t solving the $\ell_1$-norm constraint $\|\beta\|_1 \leq t$, there is a corresponding value of $\lambda$ that yields the same solution from the Lagrangian form.

In order to estimate this best value for t, artificial training and test sets can be created by splitting up the given dataset at random, and estimating performance on the test data, using cross-validation. One group may be fixed as the test set, and the remaining groups may be designed as the training set. The lasso may be applied to the training data for a range of different values, and each fitted model may be used to predict the responses in the test set, recording the mean-squared prediction errors for each value of t. This process is repeated a total number of times equal to the number of groups of data. In this way, a number of different estimates of the prediction error are obtained over a range of values of t.

The lasso problem is a quadratic problem with a convex constraint. Many sophisticated quadratic program methods exist for solving the lasso. One simple and effective computational algorithm that may be employed utilizes the criterion in Lagrangian form, namely:

$$\underset{\beta \in \mathbb{R}^p}{\text{minimize}}\left\{\frac{1}{2N}\sum_{i=1}^{N}\left(y_i - \sum_{j=1}^{p} x_{ij}\beta_j\right)^2 + \lambda\sum_{j=1}^{p}|\beta_j|\right\}.$$

It may be assumed that $y_i$ and the features $x_{ij}$ may be standardized so that:

$$\frac{1}{N}\sum_i y_i = 0, \frac{1}{N}\sum_i x_{ij} = 0, \text{ and } \frac{1}{N}\sum_i x_{ij}^2 = 1$$

and the intercept term $\beta_o$ can be omitted. The Lagrangian form is especially useful for numerical computation of the solution by a simple procedure known as coordinate descent. A simple coordinate-wise scheme for solving the lasso problem involves repeatedly cycling through the predictors in a fixed (but arbitrary) order (e.g., j=1, 2, ... p), wherein at the $j^{th}$ step, the coefficient $\beta_j$ is updated by minimizing the objective function in this coordinate while holding fixed all other coefficients $\{\hat{\beta}_k, k \neq j\}$ at their current values.

If the Lagrangian form objective is rewritten as:

$$\frac{1}{2N}\sum_{i=1}^{N}\left(y_i - \sum_{k \neq j} x_{ik}\beta_k - x_{ij}\beta_j\right)^2 + \lambda\sum_{k \neq j}|\beta_k| + \lambda|\beta_j|,$$

then the solution for each $\beta_j$ can be expressed in terms of the partial residual $r_i^{(j)} = y_i - \sum_{k \neq j} x_{ik}\hat{\beta}_k,$ which removes, from the outcome, the current fit from all but the $j^{th}$ predictor. In terms of this partial residual, the $j_{th}$ coefficient is updated as:

$$\hat{\beta}_j = S_\lambda\left(\frac{1}{N}\langle x_j, r^{(j)}\rangle\right).$$

(In the preceding equation, $S_\lambda$ represents a soft-thresholding operation $S_\lambda(x)$ that translates its argument x toward zero by the amount A and sets it to zero if $|x| \leq \lambda$.) Equivalently, the update can be written as:

$$\hat{\beta}_j \leftarrow S_\lambda\left(\hat{\beta}_j + \frac{1}{N}\langle x_j, r\rangle\right),$$

where the full residuals are:

$$r_i = y_i - \sum_{j=1}^{p} x_{ij}\hat{\beta}_j.$$

The numerical computation algorithm operates by applying this soft-thresholding update repeatedly in a cyclical manner, updating the coordinates of $\hat{\beta}$ (and therefore the residual vectors) along the way. Such algorithm corresponds to the method of cyclical coordinate descent, which minimizes the convex objective along each coordinate at a time. Under relatively mild conditions, such coordinate-wise minimization schemes applied to a convex function converge to a global optimum.

In other embodiments, a method of pathwise coordinate descent may be used to compute a lasso solution not only for a single fixed value of $\lambda$, but rather an entire path of solutions over a range of possible $\lambda$ values. Such a method may begin with a value of $\lambda$ just large enough that the only optimal solution is the all-zeroes vector, and then repeatedly decreasing $\lambda$ by a small amount and running coordinate descent until convergence.

In certain embodiments, one or more routines or algorithms of the predictive software model may be implemented in R programming language, which is an open source programming language and software environment. R is a GNU package that is supported by the R Foundation for Statistical Computing (Vienna, Austria). If desired, other programming languages or software environments may be employed.

FIG. 1 is a high-level schematic diagram of operation of an algorithm 10 for automatically extracting laboratory-implemented features 20 that capture irregularities in patient speech samples, and that are supplied to a decision engine 26 (or other processor circuitry) that may further receive corresponding subjective expert (e.g., speech-language pathologist) ratings 24 for a plurality of perceptual dimensions of patient speech, according to one embodiment of the present disclosure. EMS features 12, LTAS features 14, spatio-temporal features 16, and dysphonia features 18 are identified from a database 11 of dysarthric speech samples, with outputs supplied to the decision engine 26. Subjective expert ratings 24 corresponding to the extracted set of laboratory-implemented features 20 are also supplied from an SLP ratings database 22.

As noted previously, existing objective measures in speech and language clinics focus on measuring aspects of speech signals that are not interpretable in clinical settings. Examples of such objective measures include instruments that measure pitch, formants, energy, and other similar metrics.

In contrast to these existing objective measures in speech and language clinics, embodiments according to the present disclosure are useful for bridging the subjective-objective divide by blending the face validity of perceptual assessment with the reliability of objective measures. Advances in signal processing and machine-learning in conjunction with the present disclosure are leveraged to model expert perceptual judgments, and to facilitate predictive software modeling of perceptual ratings of speech. Comparisons of outcomes between laboratory data and those collected in clinical settings inform the theories that support the model with real-world data. Technical capabilities will advance with the refinement of the speech algorithms to optimize their performance. Technology that affords stable objective measures of speech that map to expert perceptual ratings is anticipated to have high clinical impact. In particular, systems and methods disclosed herein may offer a platform to sensitively assess treatment efficacy, disease onset, and disease progression, etc. with unbiased perception-calibrated metrics.

While acoustic analysis of disordered speech is commonplace in research, technology has yet to be developed that adds clinical value. The approach disclosed herein is novel in several ways.

In certain embodiments, signal processing capabilities and machine learning algorithms may be leveraged to model (weighted) perceptions of experts (e.g., speech-language pathologists) in the generation and use of a predictive software model. Thus, the output of the predictive software model is immediately clinically transparent, and does not require any norms or references for comparison.

In certain embodiments, predictive software models disclosed herein are "learners," meaning that the algorithms become more refined with each iteration.

In certain embodiments, systems and methods disclosed herein may be integrated in a telehealth platform. This would be transformative by expanding videoconference capabilities of current remote methods to provide analytical capabilities.

Figure 2:
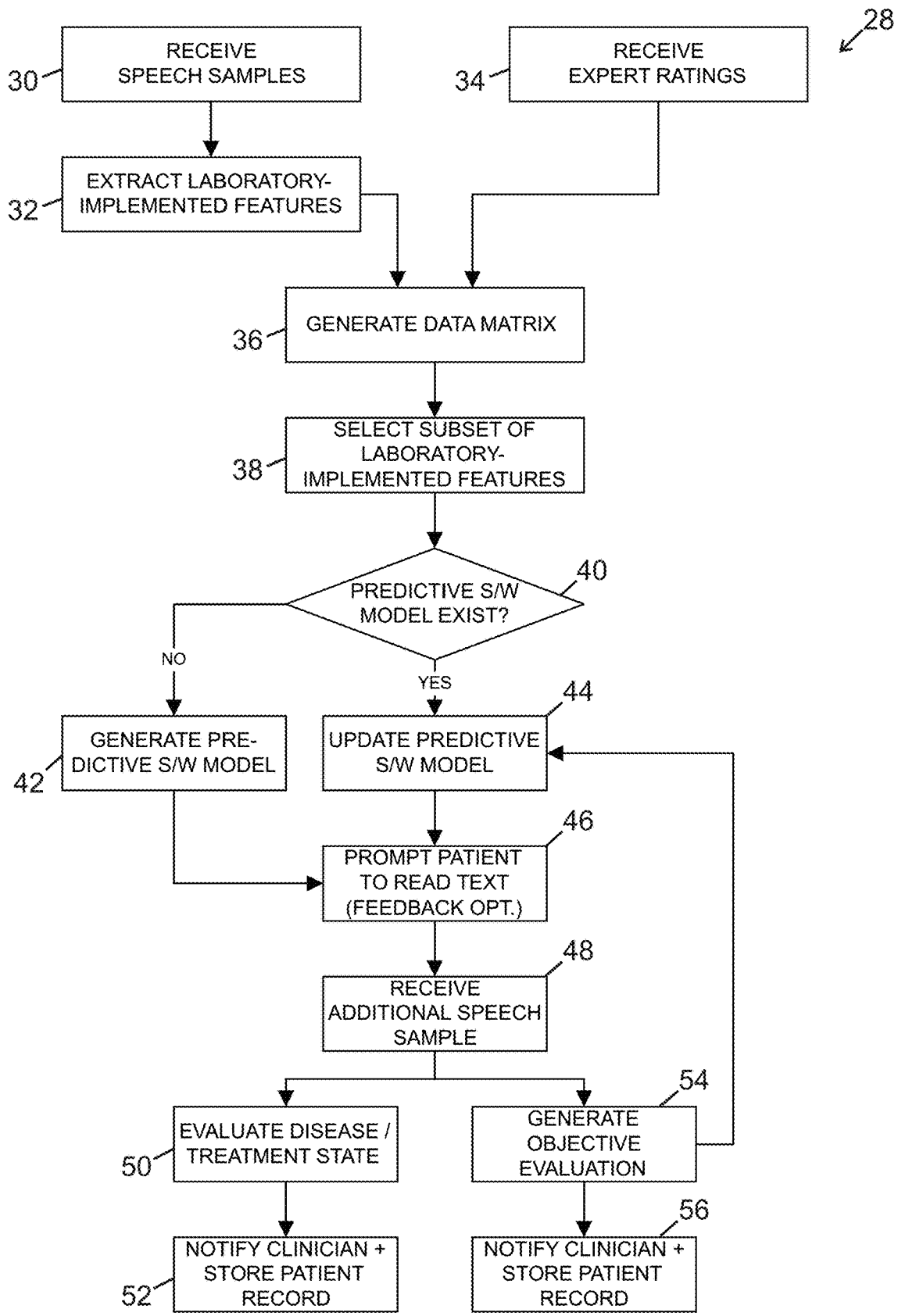
FIG. 2 is a flowchart outlining steps in a method for evaluating speech including generation and use of a software model in which laboratory-implemented features that capture irregularities in speech are selected and used to predict five commonly assessed perceptual dimensions (nasality, prosody, articulatory precision, vocal quality, and severity) for objective evaluation of the perceptual dimensions and/or evaluation of at least one of disease onset, disease progression, or disease treatment efficacy for a condition involving dysarthria as a symptom, according to one embodiment of the present disclosure.

FIG. 2 is a flowchart outlining steps in a method 28 for evaluating speech, including generation and use of a software model in which laboratory-implemented features that capture irregularities in the speech are selected and used to predict five commonly assessed perceptual dimensions (nasality, prosody, articulatory precision, vocal quality, and severity) for objective evaluation of the perceptual dimensions and/or evaluation of at least one of disease onset, disease progression, or disease treatment efficacy for a condition involving dysarthria as a symptom, according to one embodiment of the present disclosure. The method 28 includes receiving speech samples according to step 30 (e.g., speech samples for multiple patients exhibiting dysarthria), extracting laboratory-implemented features according to step 32 (e.g., an envelope modulation spectrum, a long-term average spectrum, spatio-temporal features, and dysphonia features) from the received speech samples, and supplying the laboratory-implemented features to generate a data matrix according to step 36. A parallel step includes receiving subjective multi-point (e.g., 7 point) ratings according to step 34 generated by experts (e.g., speech-language pathologists) for the same speech samples as used in steps 30, 32, and supplying the ratings to the data matrix. Thereafter, the method includes selecting a subset of a plurality of laboratory-implemented features according to step 38 from the data matrix, wherein the subset of the plurality of laboratory-implemented features is relevant for predicting the plurality of perceptual dimensions, and preferably also reduces multi-collinearity. In certain embodiments, the subset of features may be down-selected and centered. According to decision block 40, if a predictive software model has not yet been created, then a predictive software model (e.g., an objective evaluation linear model) is created at step 42; otherwise, a pre-existing predictive software model is updated according to step 44. In certain embodiments, selection of the subset of the plurality of laboratory-implemented features relevant to prediction of the plurality of perceptual dimensions may include the use of lasso or $\ell_1$-regularized regression, or more specifically the use of a combination of cross-validation and sparsity-based feature selection. Following generating or updating of the predictive software model, an additional patient speech sample may be obtained for processing with the predictive software model. According to step 46, a patient may be prompted (e.g., by a visual display device) to read text, optionally in conjunction with the provision to the patient of user-perceptible (e.g., tactile, visible, auditory, or the like) feedback while the at least one patient reads the displayed text, to alert the patient to attainment of one or more conditions indicative of a speech problem. Upon generation of the additional speech sample, such sample may be received (e.g., electronically received) by a speech evaluation system incorporating the predictive software model according to step 48. Operation of the predictive software model on the additional speech sample may result in one or more of (a) generating an objective evaluation of the plurality of perceptual dimensions utilizing the at least one additional patient speech sample, according to step 54; or (b) evaluating disease and/or treatment state (e.g., at least one of disease onset, disease progression, or disease treatment efficacy) for a condition involving dysarthria as a symptom, according to step 50. With respect to performance of the steps of either or both of steps 50, 54, a clinician may be notified of the result of the evaluation and an electronic patient record may be stored or updated according to steps 52, 66. Moreover, following performance of the step of step 54, results of the objective evaluation of the plurality of perceptual dimensions utilizing the at least one additional patient speech sample may be supplied to the predictive software model to enable the model to be updated, by returning to step 44.

Figure 3:
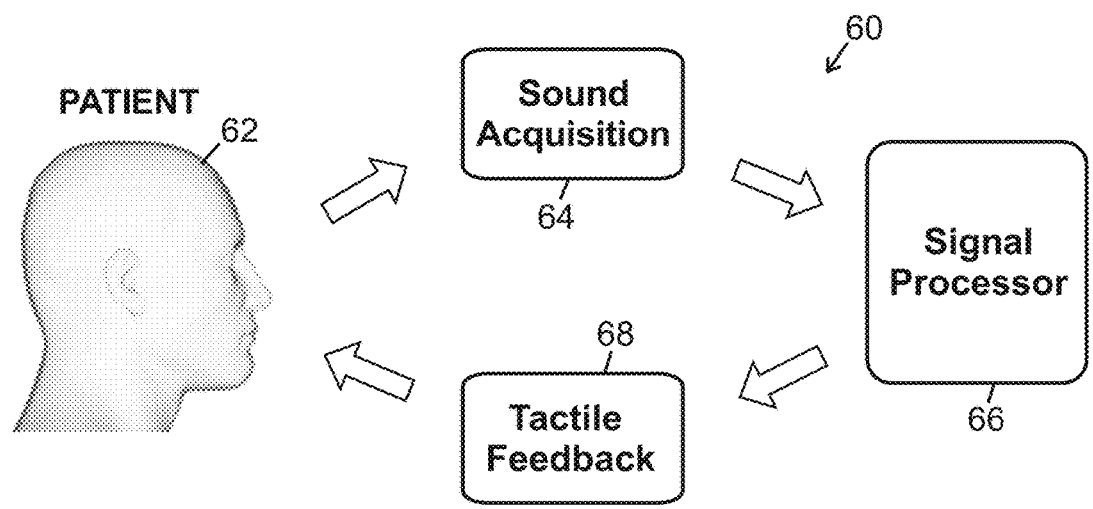
FIG. 3 is a schematic showing a speech sample (sound) acquisition module, a tactile feedback module, and a signal processing module ("signal processor", e.g., for objective feature extraction) that may be used with a patient as components of a sample acquisition subsystem useful with one or more embodiments disclosed herein.

FIG. 3 is a schematic showing a speech sample (e.g., sound) acquisition module 64, a tactile feedback module 68, and a signal processing module 66 ("signal processor", e.g., for objective feature extraction) that may be used with a patient 62 as components of a sample acquisition subsystem 60 useful with one or more embodiments disclosed herein. The sound acquisition module 64 may embody a microphone (or similar transducer) or a signal receiver for receiving speech (or a signal indicative of speech) from the patient 62 and for producing (or receiving) a speech sample as an analog electrical signal, which may be digitized thereafter for subsequent processing. The sound acquisition module 64 is operatively coupled with the signal processing module 66, which may be used to (a) determine whether a speech error is present, and/or (b) process the received speech sample according to any suitable processing steps disclosed herein. The signal processing module 66 may further make decisions as to what types of alert signal(s) should be presented to the user, and may further log details corresponding to alerts and/or audio sample status. The tactile feedback module 68 may further be arranged to receive one or more speech error signals from the signal processing module 66, and provide a user-perceptible alert signal to the patient 62.

Figure 4:
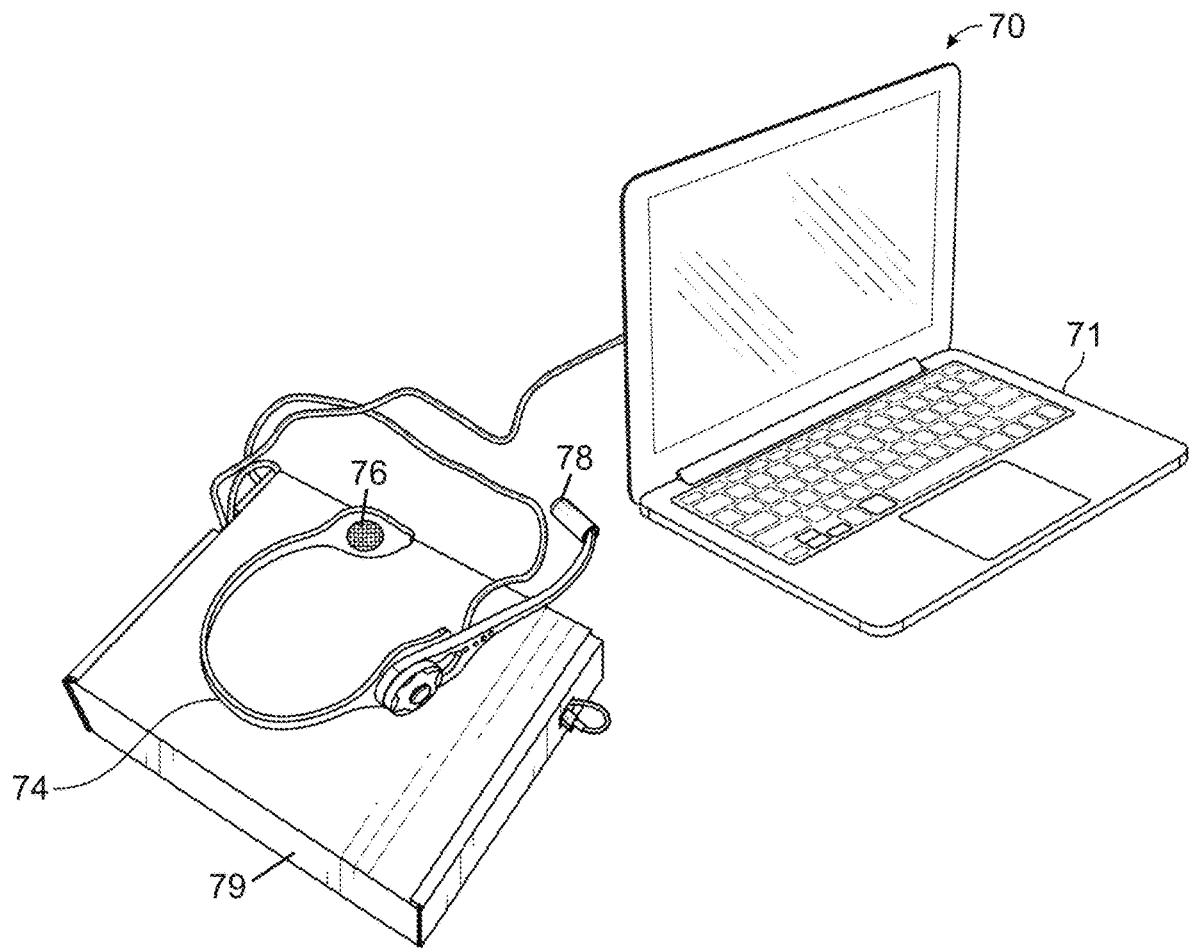
FIG. 4 illustrates components of an exemplary speech evaluation system comprising a laptop computer, a headset, and a signal processing module, according to one embodiment of the present disclosure.

FIG. 4 illustrates components of an exemplary speech evaluation system 70 comprising a laptop computer 71, a headset 74, and a signal processing module 79, according to one embodiment of the present disclosure. The headset 74 includes ear-contacting portions 76 and a close-talk microphone 78. The signal processing module 79 includes a STEVAL-CCA023V1 demonstration board (STMicroelectronics, Geneva, Switzerland). To provide tactile feedback, the headset 74 may include a linear resonant actuator and a DRV2605EVM-CT driver board (Texas Instruments, Dallas, Tex.). In certain embodiments, tactile feedback may be provided to a patient while supplying a speech sample via the close-talk microphone 78 to components of the speech evaluation system 70. While a separate signal processing module 79 is shown in FIG. 4 as intermediately arranged between the headset 74 and the laptop computer 71, in certain embodiments, the headset 74 may be coupled directly to the laptop computer 71 without requiring a dedicated signal processing module 79. In certain embodiments, some or all of the method steps described in connection with FIG. 2 may be performed using the speech evaluation system 70. The laptop computer 71 includes a non-transient computer readable medium such as a hard disk drive. The non-transient computer readable medium may include program instructions for causing the laptop computer 71 to perform method steps such as described in connection with FIG. 2 or otherwise disclosed herein. A display of the laptop computer 71 may be used to display text and instructions to prompt a patient to supply one or more speech samples to the headset 74 for capture and use by the speech evaluation system 70.

Figure 5:
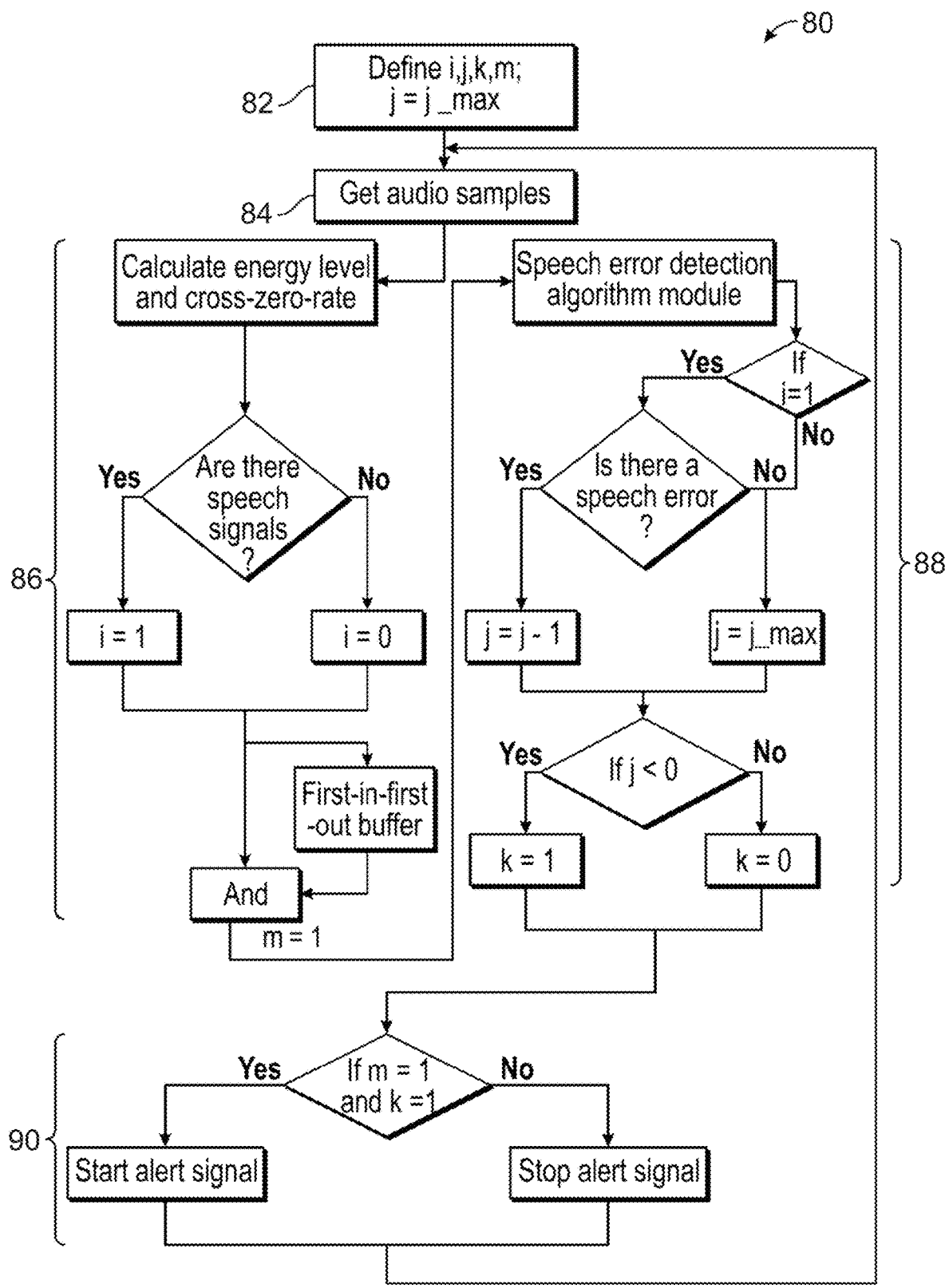
FIG. 5 is flow chart depicting a method of monitoring and detecting errors in audio signals containing speech and providing a user-perceptible alert signal, as may be used in obtaining speech samples for use with one or more embodiments disclosed herein.

FIG. 5 is a flow chart depicting a method 80 for eliciting and monitoring speech provided by a patient and providing a user-perceptible alert signal, which may be used for therapeutic treatment. The method 80 comprises an alert delay algorithm provided by a processor in a time domain. Although the term "processor" is used in a singular sense, it is to be appreciated that in certain embodiments, multiple processors may be employed, and optionally may be associated with different electronic (e.g., computing) devices. In step 82, the processor is configured to define, or receive definitions for, variables i, j, k, m. In particular, the processor initially sets a counter j to a maximum value (e.g., j=j_max). In step 84, the processor is configured to receive audio samples. The processor is configured to monitor audio samples associated with the speech. In particular, in steps 86, the processor detects whether the audio samples contain speech signals by calculating energy level and cross-zero-rate, and in steps 88, the processor determines whether a speech error is present through a speech error detection algorithm module (e.g., the speech level is below the volume level threshold, or another speech error condition is present). In certain embodiments, the processor may monitor multiple (e.g., 10, 20, 30, 40, 50 or more) audio samples per second and provide a multi-second (e.g., 2, 3, 4, 5, 6, 7, 8, 9, or 10 second) delay for the time interval before providing an alert signal. In the embodiment depicted in FIG. 5, the maximum value of the counter j is set to 250. In steps 88, if a speech error is detected, then the counter decrements by 1 for each consecutive audio sample in which the speech level is below the volume level threshold. In steps 90, when the counter reaches zero or a negative value, the processor provides the alert signal. In other words, when the processor detects speech signals in steps 86 (e.g., i=1), those speech signals are processed through a first-in-first-out buffer (e.g., m=1), and when a speech error has been consistently detected (j<0; k=1) then the processor initiates an alert signal. The processor may terminate the alert signal if one or more of the foregoing conditions cease to be true.

Figure 6:
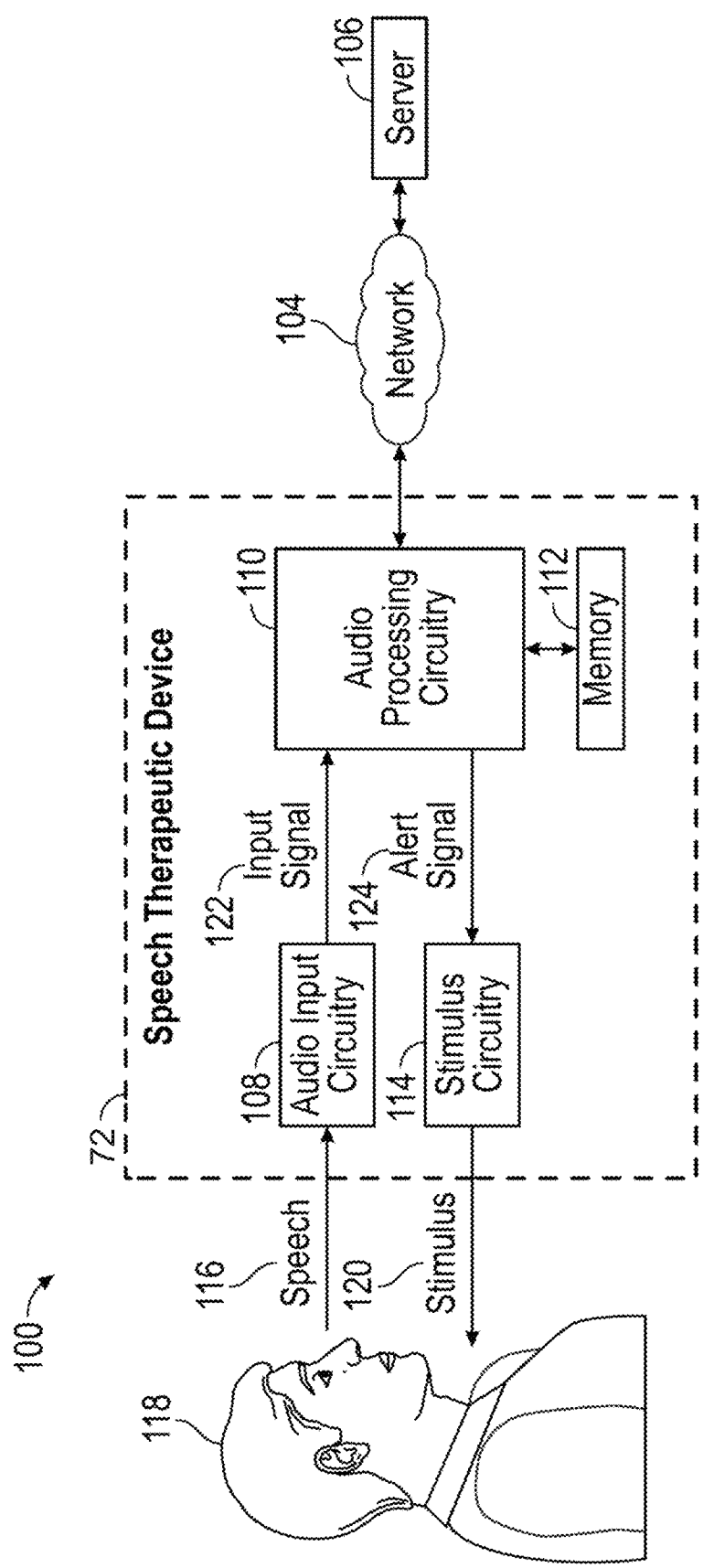
FIG. 6 is a schematic showing interconnections between components of an exemplary speech evaluation system, including speech sample acquisition, processing circuitry, and network elements that may be used in one or more embodiments disclosed herein.

FIG. 6 is a schematic showing interconnections between components of a speech evaluation system 100 including a speech therapeutic device 72, processing circuitry 110 (with associated memory 112), a network 104, and a server 106. The speech therapeutic device 72 includes audio input circuitry 108 and stimulus circuitry 114. The audio input circuitry 108 and stimulus circuitry 114 may be coupled with the processing circuitry 110 via wired connections, wireless connections, or a combination thereof. The speech therapeutic device 72 may further comprise a behind-the-ear device, an ear-mold device, a headset, a headband, a smartphone, or a combination thereof. The speech therapeutic device 72 may be configured to receive speech 116 from a patient 62 and provide a stimulus 120 to the patient 62 based on processing of the speech 116.

The audio input circuitry 108 may include at least one microphone. In certain embodiments, the audio input circuitry 108 may include a bone conduction microphone, a near field air conduction microphone array, or a combination thereof. The audio input circuitry 108 may be configured to provide an input signal 122 that is indicative of the speech 116 provided by the patient 62 to the processing circuitry 110. The input signal 122 may be formatted as a digital signal, an analog signal, or a combination thereof. In certain embodiments, the audio input circuitry 108 may provide the input signal 122 to the processing circuitry 110 over a personal area network (PAN). The PAN may comprise Universal Serial Bus (USB), IEEE 1394 (FireWire) Infrared Data Association (IrDA), Bluetooth, ultra-wideband (UWB), Wi-Fi Direct, or a combination thereof. The audio input circuitry 108 may further comprise at least one analog-to-digital converter (ADC) to provide the input signal 122 in digital format.

The processing circuitry 110 may include a communication interface (not shown) coupled with the network 104 and a processor (e.g., an electrically operated processor (not shown) configured to execute a pre-defined and/or a user-defined machine readable instruction set, such as may be embodied in computer software) configured to receive the input signal 122. The communication interface may include circuitry for coupling to the PAN, a local area network (LAN), a wide area network (WAN), or a combination thereof. The processing circuitry 110 is configured to communicate with the server 106 via the network 104. In certain embodiments, the processing circuitry 110 may include an ADC to convert the input signal 122 to digital form. In other embodiments, the processing circuitry 110 may be configured to receive the input signal 122 from the PAN via the communication interface. The processing circuitry 110 may further comprise level detect circuitry, adaptive filter circuitry, voice recognition circuitry, or a combination thereof. The processing circuitry 110 may be further configured to process the input signal 122 and to provide an alert signal 124 to the stimulus circuitry 114.

The processor may be further configured to generate a record indicative of the alert signal 124. The record may comprise a rule identifier and an audio segment indicative of the speech 116 provided by the patient 62. In certain embodiments, the audio segment may have a total time duration of at least one second before the alert signal 124 and at least one second after the alert signal 124. Other time intervals may be used. For example, in other embodiments, the audio segment may have a total time duration of at least three seconds, at least five seconds, or at least ten seconds before the alert signal 124 and at least three seconds, at least five seconds, or at least ten seconds after the alert signal 124. In other embodiments, at least one reconfigurable rule may comprise a pre-alert time duration and a post-alert time duration, wherein the audio segment may have a total time duration of at least the pre-alert time duration before the alert signal 124 and at least the post-alert time duration after the alert signal 124. In certain embodiments, the foregoing audio segments may be used as patient speech samples according to speech evaluation systems and methods disclosed herein. By identifying conditions indicative of speech errors in speech samples, samples exhibiting indications of dysarthria may be identified (e.g., flagged) and preferentially stored, aggregated, and/or used by a speech evaluation system.

A record corresponding to a speech sample may optionally include a location identifier, a time stamp, or a combination thereof indicative of the alert signal 124. The location identifier may comprise a Global Positioning System (GPS) coordinate, a street address, a contact name, a point of interest, or a combination thereof. In certain embodiments, a contact name may be derived from the GPS coordinate and a contact list associated with the patient 62. The point of interest may be derived from the GPS coordinate and a database including a plurality of points of interest. In certain embodiments, the location identifier may be a filtered location for maintaining the privacy of the patient 62. For example, the filtered location may be "user's home", "contact's home", "vehicle in transit", "restaurant", or "user's work". In certain embodiments, the at least one reconfigurable rule may comprise a location type, wherein the location identifier is formatted according to the location type.

The processing circuitry 110 is configured to communicate with the memory 112 for storage and retrieval of information, such as subroutines and data utilized in predictive software models—including (but not limited) to patient speech samples, subjective expert ratings corresponding to patient speech samples, and subsets of laboratory-implemented features. The memory 112 may be a non-volatile memory, a volatile memory, or a combination thereof. The memory 112 may be wired to the processing circuitry 110 using an address/data bus. In certain embodiments, the memory 112 may be a portable memory coupled with the processor via the PAN.

The processing circuitry 110 may be further configured to transmit one or more records via the network 104 to the server 106. In certain embodiments, the processor may be further configured to append a device identifier, a user identifier, or a combination thereof to the record. A device identifier may be unique to the speech therapeutic device 72, and a user identifier may be unique to the patient 62. The device identifier and the user identifier may be useful to a speech-language pathologist or other speech therapeutic professional, wherein the patient 62 may be a patient of the pathologist or other professional.

The stimulus circuitry 114 is configured to receive the alert signal 124 and may comprise a vibrating element, a speaker, a visual indicator, or a combination thereof. In certain embodiments, the alert signal 124 may encompass a plurality of alert signals including a vibrating element signal, a speaker signal, a visual indicator signal, or a combination thereof. In certain embodiments, a speaker signal may include an audio signal, wherein the processing circuitry 110 may provide the audio signal as voice instructions for the patient 62.

The network 104 may comprise a PAN, a LA), a WAN, or a combination thereof. The PAN may comprise Universal Serial Bus (USB), IEEE 1394 (FireWire) Infrared Data Association (IrDA), Bluetooth, ultra-wideband (UWB), Wi-Fi Direct, or a combination thereof. The LAN may include Ethernet, 802.11 WLAN, or a combination thereof. The network 104 may also include the Internet. The server 106 may comprise a personal computer (PC), a local server connected to the LAN, a remote server connected to the WAN, or a combination thereof. In certain embodiments, the server 106 may be a software-based virtualized server running on a plurality of servers.

As used herein, the term "audio sample" may refer to a single discrete number associated with an amplitude at a given time. Certain embodiments may utilize a typical audio sampling rate of 8 kHz or 44.1 kHz. As used herein, the term "audio signal frame" may refer to a number of consecutive audio signal samples. In certain embodiments, a typical length of time associated with an audio signal frame may be in a range of from 20 ms to 50 ms. For an audio signal frame of 20 ms at an 8 kHz sampling rate, and for an audio clip of one second, there are $\frac{1}{20}$ ms=50 frames, and for each frame there are 8000/50=40 samples.

Figure 7A:
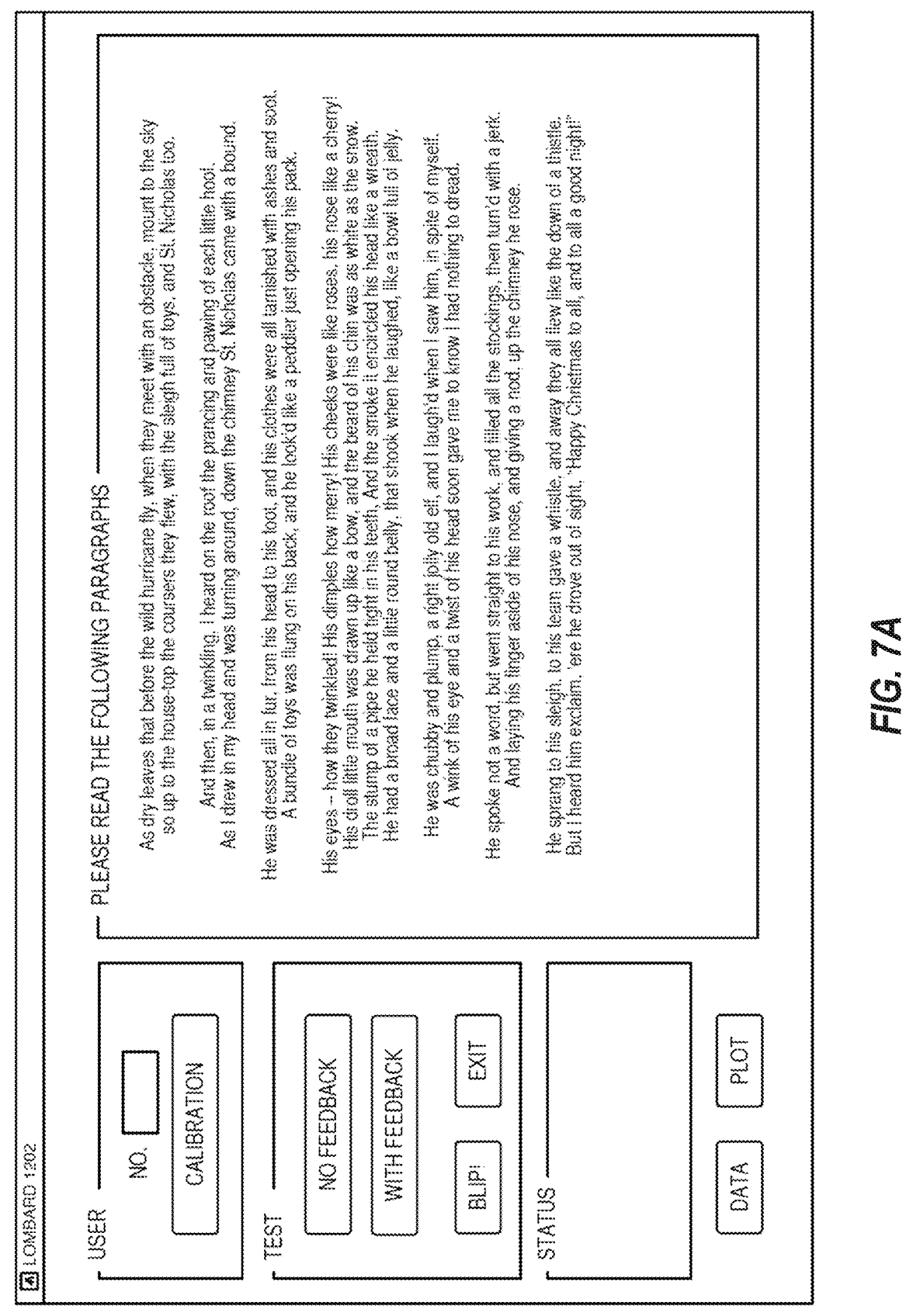

FIG. 7A illustrates a first graphical user interface screen for a speech evaluation system. As shown, a user is prompted to read various paragraphs of displayed text, either with or without feedback (e.g., tactile, auditory, and/or visual feedback). Data including conditions indicative of speech errors or other events may be recorded and/or plotted.

Figure 7B:
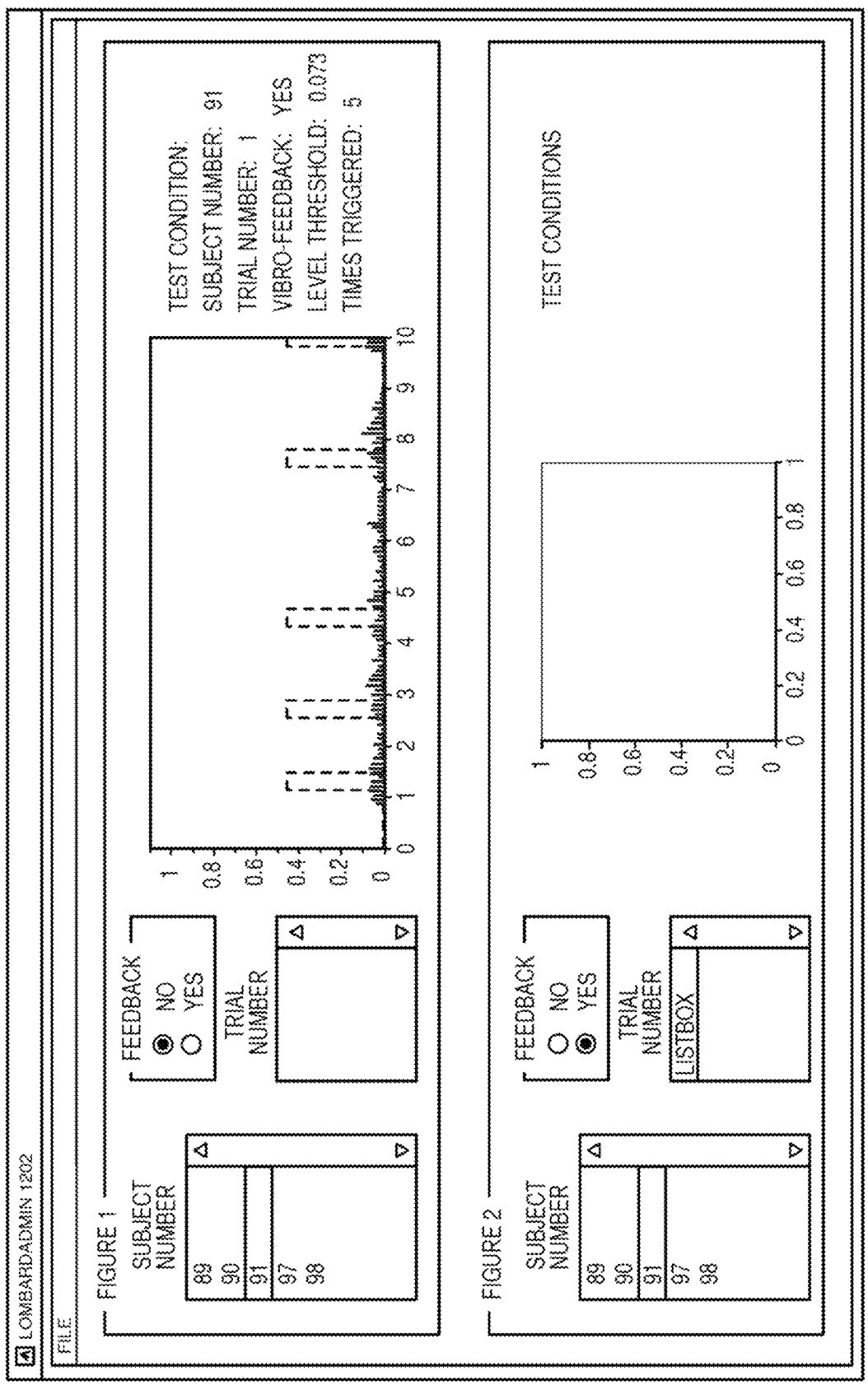
FIG. 7B illustrates a second graphical user interface screen for permitting a speech-language pathologist (or other clinician) to administer or review a speech sample for use with the speech evaluation system of FIG. 7A, according to one embodiment of the present disclosure.

FIG. 7B illustrates a second graphical user interface screen for a speech evaluation system, including upper and lower frames relating to an audio file generated by a user reading the displayed text shown in FIG. 7A. The upper frame of FIG. 7B graphically displays five events signifying actual or potential speech errors (identified by rectangles overlying the speech waveform). The lower frame of FIG. 7B enables display of additional information concerning speech analysis.

Figure 8:
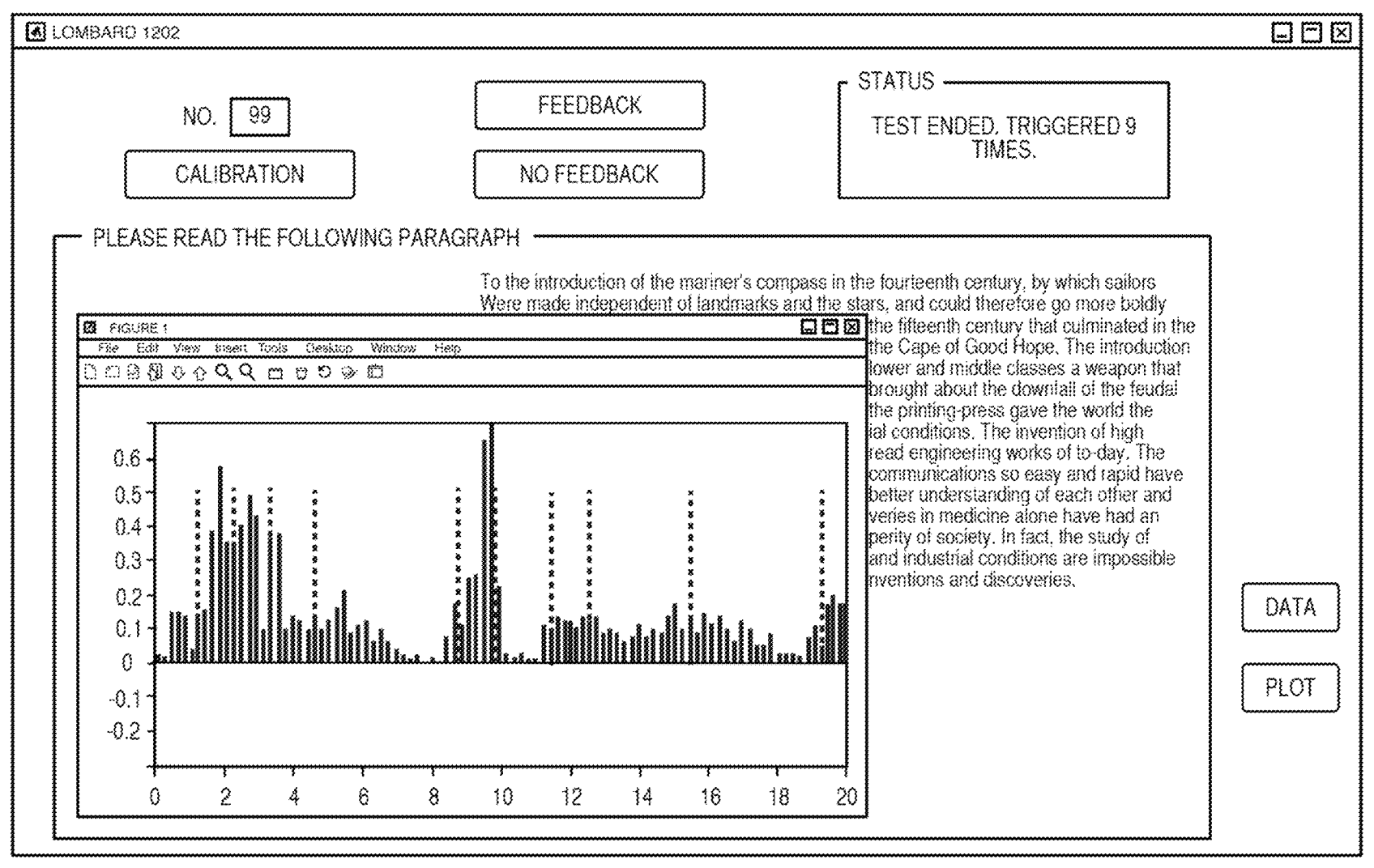

FIG. 8 illustrates superimposed third and fourth graphical user interface screens for a speech evaluation system, including a background frame prompting a user to read various paragraphs of displayed text (either with or without feedback) and including a superimposed foreground frame graphically displaying multiple events signifying actual or potential speech errors (identified by narrow vertical rectangles or bars extending generally above the speech waveform).

The foregoing graphical user interface screens may be prepared using MATLAB (MathWorks, Natick, Mass.) or another suitable software.

FIG. 9 is a perspective view illustration of a behind-the-neck therapeutic headset device 170 comprising audio input and stimulus circuitry 178, and a band 176, according to one embodiment. The audio input and stimulus circuitry 178 comprises a bone conduction microphone 172 (that only picks up the voice of the wearer), and the audio input and stimulus circuitry 178 comprises a vibrating element 174. The bone conduction microphone 172 may be arranged as a right capsule 172' of the behind-the-neck therapeutic headset device 170, and may be driven by a TS472 microphone amplifier (STMicroelectronics, Geneva, Switzerland). The vibrating element 174 may be arranged as a left capsule 174' of the behind-the-neck therapeutic headset device 170 and comprises a motor. In certain embodiments, the band 176 of the behind-the-neck therapeutic headset device 170 comprises a circuit board (e.g., with a wireless module), a battery case, etc.

FIGS. 10A and 10B provide side elevation views of first and second halves 202A, 202B of a therapeutic behind-the-ear device 200. The first half 202A may be mated with the complementary second half 202B (e.g., with or without fasteners). The therapeutic behind-the-ear device 200 further comprises at least one microphone 204, a processor (e.g., a microprocessor) 206, a switch 208 (e.g., power switch), a vibrating element 210, and/or a battery 212.

Figure 11:
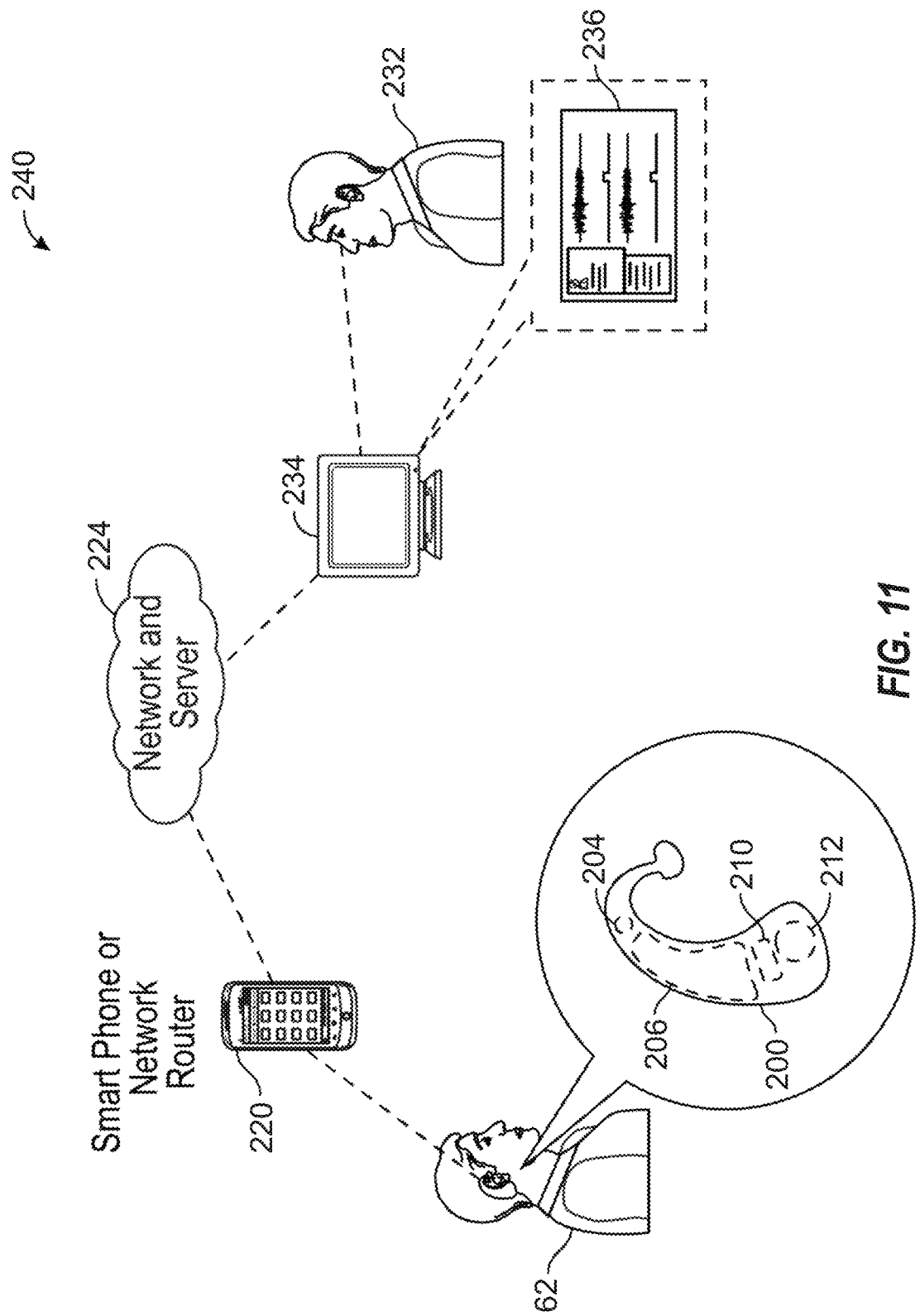
FIG. 11 is a schematic diagram of a speech evaluation system providing an interface for a speech-language pathologist via a client device, wherein a speech sample may be gathered remotely from a patient via a communication device, according to one embodiment of the present disclosure.

FIG. 11 is a diagram depicting an exemplary speech evaluation system 240 providing an interface for a speech-language pathologist 232 via a client device 234, wherein a patient 62 is a patient of the speech-language pathologist 232. The client device 234 may be a PC, a smartphone, or a tablet device. The client device 234 provides the speech-language pathologist 232 with a graphical administrator interface (GAI) portal 236, with the client device 234 optionally being remotely located from a network and server 224. In certain embodiments, the GAI portal 236 permits the speech-language pathologist 232 to monitor error patterns, communicate with the patient 62, and/or adjust a course of treatment. In certain embodiments, the speech-language pathologist 232 may be located in the presence of the therapeutic behind-the-ear device 200 and/or interact with the patient 62 or the device 200 via a wired interface or close-proximity wireless interface (e.g., BLUETOOTH® (Bluetooth Sig, Inc., Kirkland, Wash., USA) or another wireless communication protocol; not shown). In certain embodiments, the GAI portal 236 enables access to patient information and/or records indicative of problems and treatment. In certain embodiments, patient information comprises one or more of age, gender, patient identifier, device serial number, etc. In certain embodiments, the speech-language pathologist 232 may select or alter operation of the therapeutic behind-the-ear device 200 as part of a course of treatment of the patient 62 to address a dysarthric condition. As shown, the therapeutic behind-the-ear device 200 of FIGS. 10A and 10B is associated with the patient 62, wherein the therapeutic behind-the-ear device 200 includes the at least one microphone 204, the processor 206, the vibrating element 210, and the battery 212. As shown, the therapeutic behind-the-ear device 200 associated with the patient 62 is configured to communicate with a network router 220 (e.g., optionally embodied in a smartphone or other communication-enabled computing device) that is in communication with the client device 234 via the network and server 224, which may include the Internet or other desired wired and/or wireless network.

Figure 12A:
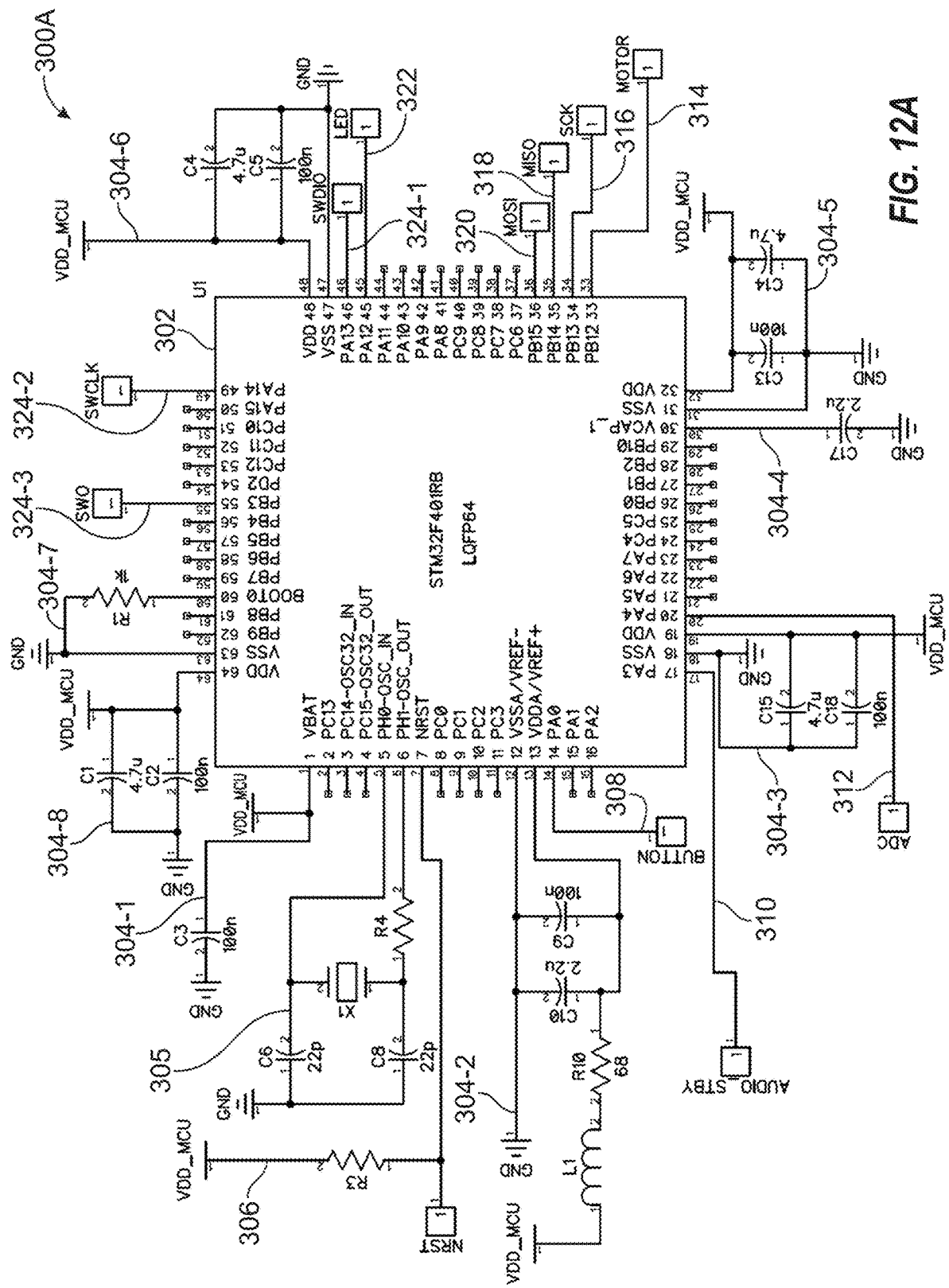
FIGS. 12A-12C are schematic diagrams of electronic circuitry according to one implementation of a speech evaluation system, according to one embodiment of the present disclosure.
Figure 12B:
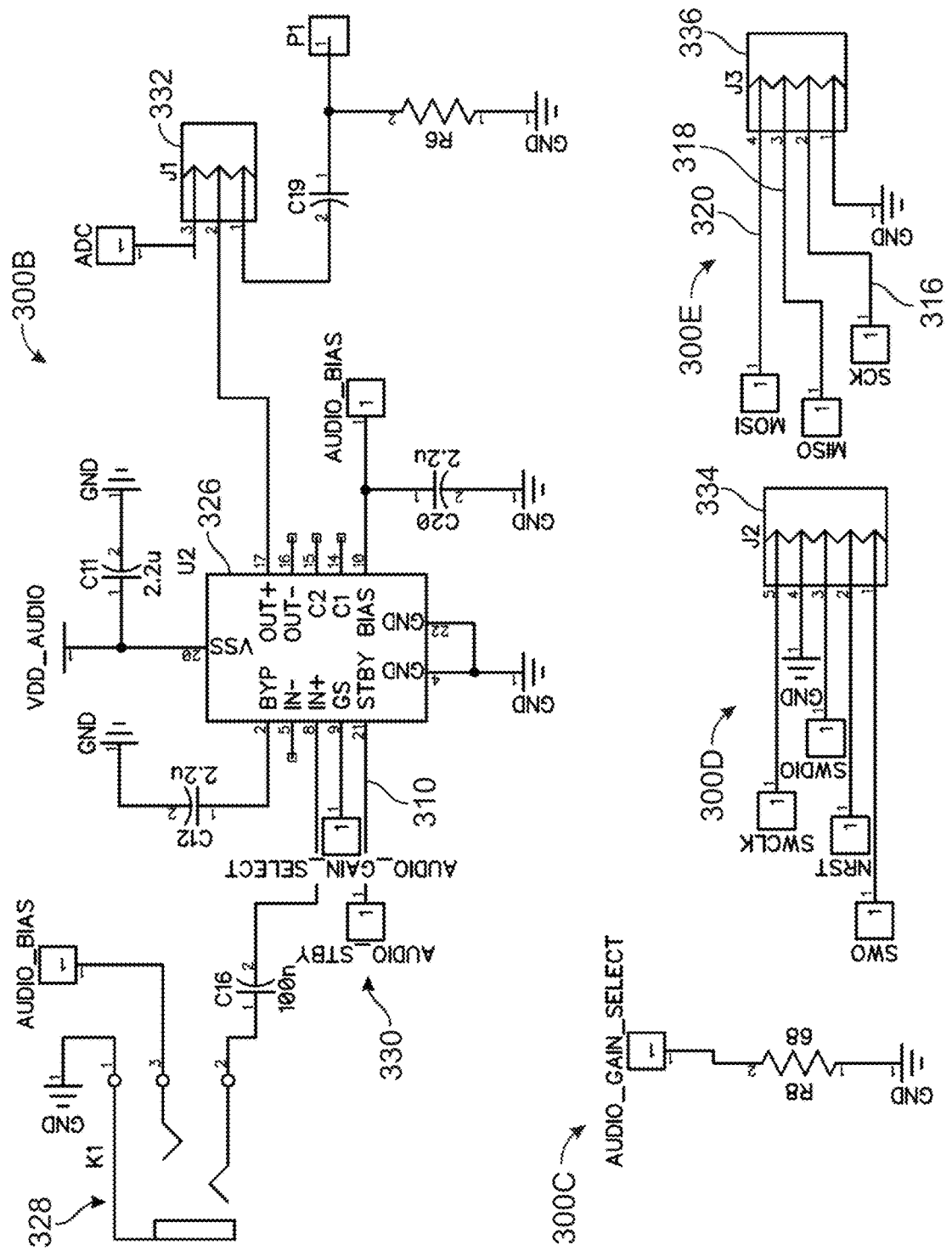
Figure 12C:
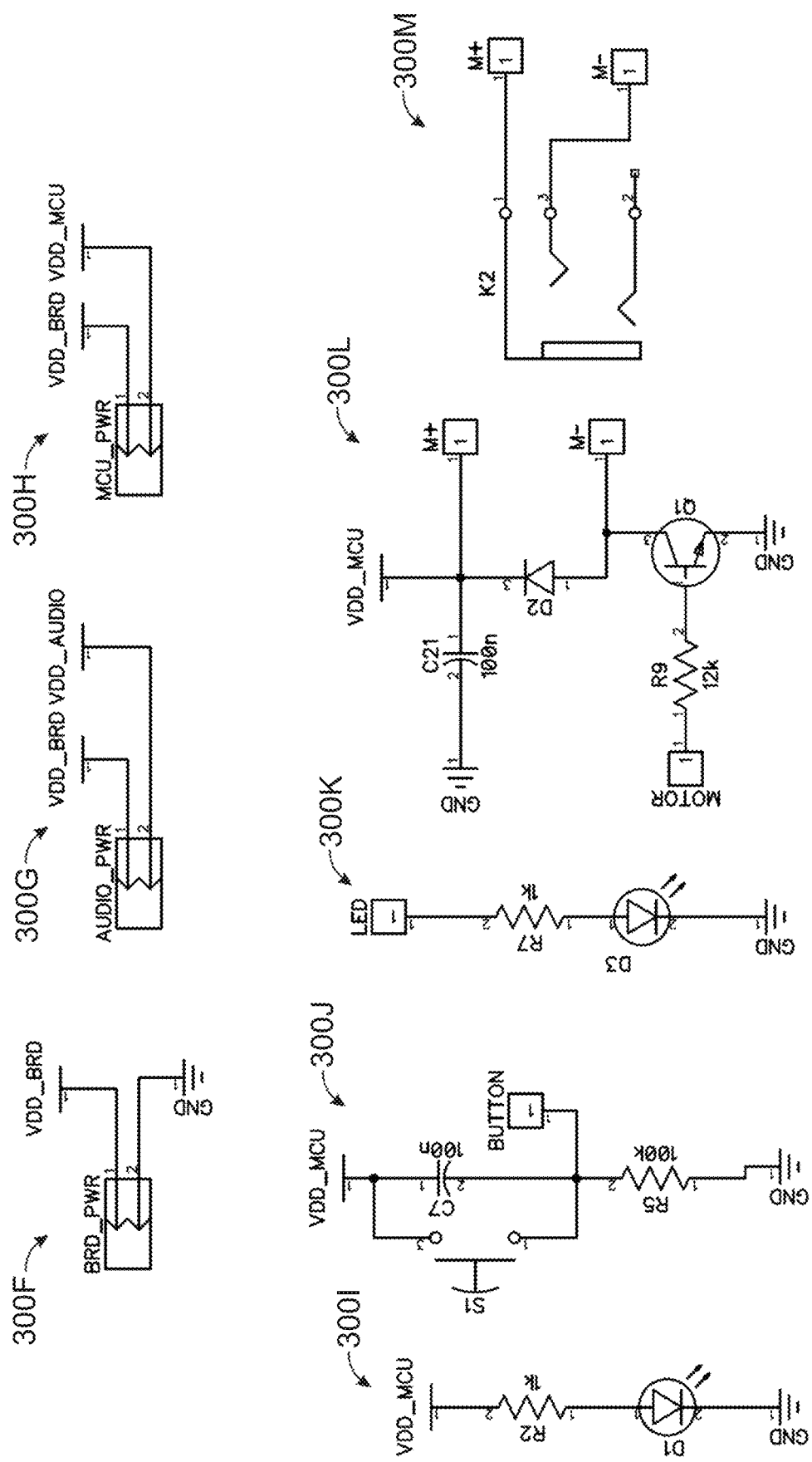

FIGS. 12A-12C are schematic diagrams of electronic circuitry 300A-300M useable with a speech evaluation device as disclosed herein. Generally, the electronic circuitry 300A-300M includes circuitry for power, analog signal processing, control (e.g., for peripheral elements such as motors, LEDs, etc.), communication, and/or debugging. Referring to FIG. 12A, main circuitry 300A includes a microprocessor 302 (e.g., optionally embodied in an ARM microcontroller with digital signal processing capability and internal memory, such as a STM32F401 RB low profile quad flat pack (LQFP) microprocessor commercially available from STMicroelectronics (Geneva, Switzerland), although other types of microprocessors could be used). As illustrated, the microprocessor 302 includes 64 pins in electrical communication with one or more external circuits and/or circuit elements. In particular, the microprocessor 302 is in electronic communication with: power-related circuitry 304-1 to 304-8; clock circuitry 305 related to a microprocessor oscillator; reset circuitry 306, and event circuitry 308 related to event triggering (e.g., which may be initiated via a button or other input device); power mode circuitry 310 related to power mode selection (e.g., to control active mode or standby mode of audio preprocessing circuitry); input circuitry 312 related to analog input, such as from an audio preprocessor; motor control circuitry 314 related to motor control (e.g., for providing vibratory or tactile stimulus to a user); clock circuitry 316 related to a clock (separate from the microprocessor clock), such as may be useful to facilitate communication with circuit elements and/or other devices; master-in slave-out (MISO) circuitry 318 and master-out slave-in (MOSI) circuitry 320 to manage inter-element communications; LED control circuitry 322 to control activation of various LEDs to indicate operating mode, to indicate operating status, and/or to facilitate system debugging; and debugging circuitry 324-1 to 324-3.

Referring to FIG. 12B, audio circuitry 300B includes an audio chip 326 configured to pre-process an audio signal before it is transmitted to the microprocessor 302 (shown in FIG. 12A; e.g., shift audio bias, increase amplitude, etc.). In particular, audio circuitry 300B includes audio input circuitry 328 (shown in FIG. 12A; e.g., audio input jack), power mode selection circuitry 330, and debugging signal header 332. Mode selection circuitry 300C enables selection of a mode of the microprocessor 302 (e.g., action, standby, etc.), and may provide pinging functionality. Debugging circuitry 300D includes a debugging header 334. Communication circuitry 300E includes a communication header 336 and manages communications with various circuit elements and/or other devices.

Referring to FIG. 12C, board power circuitry 300F provides power conditioning and distribution for the circuit board. Audio power circuitry 300G provides conditioned power for audio components. MCU (microcontroller unit) power circuitry 300H provides conditioned power for the MCU. MCU power indicator circuitry 300I serves to indicate power status for the MCU (e.g., using an LED). Event circuitry 300J provides circuit triggering functionality (e.g., employing one or more user inputs). MCU state circuitry 300K serves to indicate a state for the MCU (e.g., using an LED). Motor actuation circuitry 300L serves to control actuation of at least one motor, which may provide vibratory or other tactile feedback to a user. Motor connection circuitry 300M facilitates connection and communication with a motor.

Figure 13:
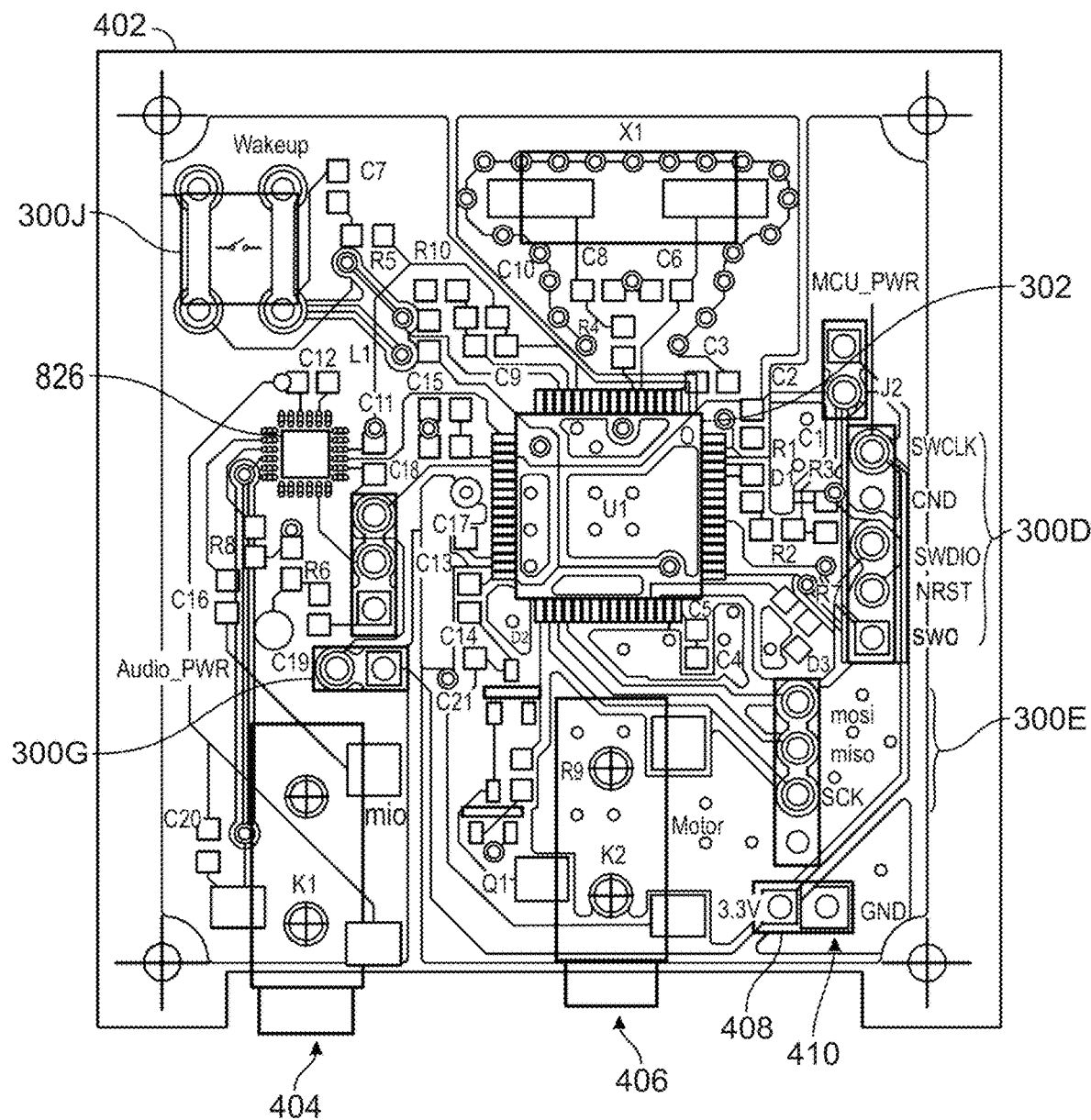
FIG. 13 is a printed circuit board (PCB) layout diagram for a signal processing module for use with a speech evaluation system according to one embodiment of the present disclosure.

FIG. 13 is a layout diagram of hardware 402 incorporating at least a portion of the electronic circuitry of FIGS. 12A-12C. As shown, the hardware 402 includes a microprocessor 302, an audio chip 326, event circuitry 300J, audio power circuitry 300G, a microphone 404, a motor 406, power input terminals 408, ground terminal 410, communication circuitry 300E, and debugging circuitry 300D. Of course, additional or fewer circuits relative to FIGS. 12A-12C may be included in the hardware 402. Exemplary length and width dimensions of the hardware 402 are about 40 mm by 40 mm. It is to be appreciated that FIGS. 12A-12C and FIG. 13 are provided for purposes of illustration only, and that numerous other implementations may embody the structures and/or provide the functionality identified in the claims.

Upon reading the foregoing description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein.

What is claimed is:

1. A method for evaluating speech in a system involving processor circuitry, the method comprising:
   selecting, by the processor circuitry, a subset of two or more laboratory-implemented features of a plurality of laboratory-implemented features from a data matrix that includes (i) the plurality of laboratory-implemented features, wherein said plurality of laboratory-implemented features is extracted from a plurality of patient speech samples, and (ii) a plurality of subjective expert ratings corresponding to the plurality of patient speech samples and involving evaluations on a multi-point scale for a plurality of perceptual dimensions including two or more of nasality, prosody, articulatory precision, vocal quality, and severity; wherein the subset of two or more laboratory-implemented features is useful for predicting the plurality of perceptual dimensions; and wherein the plurality of laboratory-implemented features comprises an envelope modulation spectrum, a long-term average spectrum, spatio-temporal features, and dysphonia features; and
   utilizing, by the processor circuitry, the subset of two or more laboratory-implemented features to generate and/or update a predictive software model configured to receive at least one additional patient speech sample and to perform at least one of the following items (a) or (b): (a) generating an objective evaluation of the plurality of perceptual dimensions utilizing the at least one additional patient speech sample; or (b) evaluating at least one of disease onset, disease progression, or disease treatment efficacy for a condition involving dysarthria as a symptom, utilizing the at least one additional patient speech sample.

2. The method of claim 1, further comprising:
   electronically receiving the plurality of patient speech samples and the plurality of subjective expert ratings; and
   extracting, by the processor circuitry, the plurality of laboratory-implemented features from the plurality of patient speech samples for inclusion in the data matrix.

3. The method of claim 1, further comprising:
   electronically receiving the at least one additional patient speech sample; and
   generating, by the processor circuitry, an objective evaluation of the plurality of perceptual dimensions utilizing the at least one additional patient speech sample.

4. The method of claim 1, further comprising:
   electronically receiving the at least one additional patient speech sample; and
   evaluating, by the processor circuitry, at least one of disease onset, disease progression, or disease treatment efficacy for a condition involving dysarthria as a symptom, utilizing the at least one additional patient speech sample.

5. The method of claim 3, further comprising prompting, by the processor circuitry, at least one patient to read displayed text prior to, or concurrently with, the electronic receiving of the at least one additional patient speech sample.

6. The method of claim 5, further comprising providing, by the processor circuitry, user-perceptible feedback to the at least one patient while the at least one patient reads the displayed text, to alert the at least one patient to attainment of one or more conditions indicative of a speech problem.

7. The method of claim 6, wherein the user-perceptible feedback comprises tactile feedback.

8. The method of claim 1, wherein the plurality of perceptual dimensions includes each of nasality, prosody, articulatory precision, vocal quality, and severity.

9. The method of claim 1, wherein the selecting of the subset of two or more laboratory-implemented features comprises use of cross-validation and sparsity-based feature selection.

10. The method of claim 1, wherein the selecting of the subset of two or more laboratory-implemented features further comprises centering data of the subset.

11. The method of claim 10, wherein the selecting of the subset of two or more laboratory-implemented features further comprises reducing the subset of two or more laboratory-implemented features to less than about 40 for each dimension of the plurality of perceptual dimensions.

12. A non-transitory computer readable medium storing software instructions that, when executed by processor circuitry of a speech evaluation system, cause the processor circuitry to carry out the method according to claim 1.

13. A system for evaluating speech, the system comprising:
   at least one memory configured to store a data matrix including (i) a plurality of laboratory-implemented features extracted from a plurality of patient speech samples and (ii) a plurality of subjective expert ratings corresponding to the plurality of patient speech samples and involving evaluations on a multi-point scale for a plurality of perceptual dimensions including two or more of nasality, prosody, articulatory precision, vocal quality, and severity; wherein the plurality of laboratory-implemented features comprises an envelope modulation spectrum, a long-term average spectrum, spatio-temporal features, and dysphonia features; and
   processor circuitry configured to (A) select a subset of two or more laboratory-implemented features of the plurality of laboratory-implemented features that is useful for predicting the plurality of perceptual dimensions, and (B) utilize the subset of two or more laboratory-implemented features to generate and/or update a predictive software model that is configured to receive at least one additional patient speech sample and is configured to perform at least one of the following items (a) or (b): (a) generate an objective evaluation of the plurality of perceptual dimensions utilizing the at least one additional patient speech sample; or (b) evaluate at least one of disease onset, disease progression, or disease treatment efficacy for a condition involving dysarthria as a symptom, utilizing the at least one additional patient speech sample.

14. The system of claim 13, wherein the processor circuitry is further configured to extract the plurality of laboratory-implemented features from the plurality of patient speech samples for inclusion in the data matrix.

15. The system of claim 13, wherein the plurality of perceptual dimensions includes each of nasality, prosody, articulatory precision, vocal quality, and severity.

16. The system of claim 13, wherein the processor circuitry is configured to select the subset of two or more laboratory-implemented features utilizing cross-validation and sparsity-based feature selection.

17. The system of claim 13, further comprising an audio input configured to electronically receive the at least one additional patient speech sample.

18. The system of claim 17, further comprising a display generator configured to provide a displayable signal prompting at least one patient to read displayed text prior to, or concurrently with, electronic reception of the at least one additional patient speech sample.

19. A system for evaluating speech, the system comprising:
at least one memory configured to store a plurality of patient speech samples and a plurality of subjective expert ratings corresponding to the plurality of patient speech samples, wherein each subjective expert rating of the plurality of subjective expert ratings includes evaluation on a multi-point scale for a plurality of perceptual dimensions including nasality, prosody, articulatory precision, vocal quality, and severity; and
processor circuitry configured to (A) extract a plurality of laboratory-implemented features from the plurality of patient speech samples to generate a data matrix, wherein the plurality of laboratory-implemented features comprises an envelope modulation spectrum, a long-term average spectrum, spatio-temporal features, and dysphonia features; (B) select a subset of two or more laboratory-implemented features useful for predicting the plurality of perceptual dimensions; and (C) generate and/or update a predictive software model that is configured to receive at least one additional patient speech sample and to perform at least one of (i) generating an objective evaluation of the plurality of perceptual dimensions utilizing the at least one additional patient speech sample or (ii) evaluating at least one of disease onset, disease progression, or disease treatment efficacy for a condition involving dysarthria as a symptom, utilizing the at least one additional patient speech sample.

20. The system of claim 19, further comprising one or more signal inputs configured to (a) electronically receive the plurality of patient speech samples, (b) electronically receive the plurality of subjective expert ratings corresponding to the plurality of patient speech samples, and (c) electronically receive the at least one additional patient speech sample.

* * * * *